(12) United States Patent
Shih et al.

(10) Patent No.: US 8,722,427 B2
(45) Date of Patent: May 13, 2014

(54) DETERMINATION OF DISSOCIATION CONSTANTS USING PIEZOELECTRIC MICROCANTILEVERS

(75) Inventors: Wan Y. Shih, Bryn Mawr, PA (US);
Joseph Capobianco, Sicklerville, NJ (US); Wei-Heng Shih, Bryn Mawr, PA (US)

(73) Assignee: Drexel University, Corporation ( * ) Notice: Subject to any disclaimer, the term of this patent is extended or adjusted under 35 U.S.C. 154(b) by 591 days.

(21) Appl. No.: 12/900,160

(22) Filed: Oct. 7, 2010

(65) Prior Publication Data

US 2011/0086435 A1   Apr. 14, 2011

Related U.S. Application Data

(60) Provisional application No. 61/249,924, filed on Oct. 8, 2009.

(51) Int. Cl.
*G01N 33/551* (2006.01)

(52) U.S. Cl.
USPC .......... 436/524; 435/6.11; 436/527; 436/806; 310/311; 310/313 R

(58) Field of Classification Search
None
See application file for complete search history.

(56) References Cited

U.S. PATENT DOCUMENTS

| | | | |
|---|---|---|---|
| 3,205,464 A | 9/1965 | Schwartz | |
| 4,093,883 A | 6/1978 | Yamamoto | |
| 4,302,694 A | 11/1981 | Fujishima et al. | |
| 4,349,762 A | 9/1982 | Kitamura et al. | |
| 4,363,993 A | 12/1982 | Nishigaki et al. | |
| 4,528,502 A | 7/1985 | Rocha | |
| 4,649,312 A | 3/1987 | Robin et al. | |
| 4,802,371 A | 2/1989 | Calderara et al. | |
| 5,054,323 A | 10/1991 | Hubbard et al. | |
| 5,313,535 A | 5/1994 | Williams | |
| 5,334,835 A | 8/1994 | Nakayama et al. | |

(Continued)

FOREIGN PATENT DOCUMENTS

| | | |
|---|---|---|
| EP | 0631319 A1 | 12/1994 |
| EP | 1536227 A2 | 6/2005 |

(Continued)

OTHER PUBLICATIONS

Amanuma, K. et al., "Crystallization behavior of sol-gel derived Pb(Zr,Ti)O3 thin films and the polarization switching effect on film microstructure", Appl. Phys. Lett., 65(24): 3140-3142 (1994).

(Continued)

*Primary Examiner* — Chris L Chin
(74) *Attorney, Agent, or Firm* — Mendelsohn, Drucker, & Dunleavy, P.C.

(57) ABSTRACT

A method for determining the dissociation constant ($K_d$) by plotting resonance frequency shift as a function of time for various target analyte concentrations. From this graph, the fraction of saturation, i.e. equilibrium fraction of bound binding sites out of all available binding sites on the sensor surface may be estimated by taking the ratio of the equilibrium resonance frequency shift at a selected concentration to the equilibrium frequency shift of the sensor. The dissociation constant is the inverse slope of the line produced by graphing the fraction of saturation as a function of concentration. This method is particularly useful for the study of protein-protein and protein-mRNA interactions.

15 Claims, 10 Drawing Sheets

(56) References Cited

U.S. PATENT DOCUMENTS

| | | | |
|---|---|---|---|
| 5,338,999 | A | 8/1994 | Ramakrishnan et al. |
| 5,382,864 | A | 1/1995 | Morikawa et al. |
| 5,445,008 | A | 8/1995 | Wachter et al. |
| 5,475,318 | A | 12/1995 | Marcus et al. |
| 5,503,010 | A | 4/1996 | Yamanaka |
| 5,553,486 | A | 9/1996 | Bonin |
| 5,626,728 | A | 5/1997 | Ramakrishnan et al. |
| 5,689,063 | A | 11/1997 | Fujiu et al. |
| 5,719,324 | A | 2/1998 | Thundat et al. |
| 5,780,727 | A | 7/1998 | Gimzewski et al. |
| 5,807,758 | A | 9/1998 | Lee et al. |
| 5,866,807 | A | 2/1999 | Elings et al. |
| 5,874,126 | A | 2/1999 | Kahn et al. |
| 5,948,993 | A | 9/1999 | Ting et al. |
| 5,966,787 | A | 10/1999 | Nakayama et al. |
| 5,996,412 | A | 12/1999 | Hansen |
| 6,075,585 | A | 6/2000 | Minne et al. |
| 6,278,379 | B1 | 8/2001 | Allen et al. |
| 6,280,396 | B1 | 8/2001 | Clark |
| 6,289,717 | B1 | 9/2001 | Thundat et al. |
| 6,336,366 | B1 | 1/2002 | Thundat et al. |
| 6,422,069 | B1 | 7/2002 | Shimizu et al. |
| 6,458,327 | B1 | 10/2002 | Vossmeyer et al. |
| 6,465,368 | B2 | 10/2002 | Inoue et al. |
| 6,589,727 | B1 | 7/2003 | Klenerman et al. |
| 6,621,080 | B2 | 9/2003 | Yamamoto |
| 6,734,425 | B2 | 5/2004 | Hantschel et al. |
| 6,781,285 | B1 | 8/2004 | Lazarus et al. |
| 6,903,491 | B2 | 6/2005 | Irie et al. |
| 6,992,421 | B2 | 1/2006 | Ikeda et al. |
| 7,055,378 | B2 | 6/2006 | Su et al. |
| 7,083,270 | B2 | 8/2006 | Torii et al. |
| 7,084,554 | B2 | 8/2006 | Xu et al. |
| 7,104,134 | B2 | 9/2006 | Amano et al. |
| 7,195,909 | B2 | 3/2007 | Klenerman et al. |
| 7,263,874 | B2 | 9/2007 | Fitch et al. |
| 7,458,265 | B2 | 12/2008 | Shih et al. |
| 7,497,133 | B2 | 3/2009 | Shih et al. |
| 7,744,713 | B2 | 6/2010 | Blessing |
| 7,744,773 | B2 | 6/2010 | Shih et al. |
| 7,942,056 | B2 | 5/2011 | Mutharasan et al. |
| 7,992,431 | B2 | 8/2011 | Shih et al. |
| 2002/0094528 | A1 | 7/2002 | Salafsky |
| 2002/0117659 | A1 | 8/2002 | Lieber et al. |
| 2002/0155303 | A1 | 10/2002 | Wielstra et al. |
| 2003/0032293 | A1 | 2/2003 | Kim et al. |
| 2003/0068655 | A1 | 4/2003 | Bottomley et al. |
| 2003/0194697 | A1 | 10/2003 | Klenerman et al. |
| 2003/0224551 | A1 | 12/2003 | Kim et al. |
| 2003/0235681 | A1 | 12/2003 | Sebastian et al. |
| 2004/0022677 | A1 | 2/2004 | Wohlstadter et al. |
| 2004/0023413 | A1* | 2/2004 | Opalsky ............... 436/518 |
| 2004/0265664 | A1 | 12/2004 | Badding et al. |
| 2005/0112621 | A1 | 5/2005 | Kim et al. |
| 2005/0114045 | A1 | 5/2005 | Giurgiutiu et al. |
| 2005/0199047 | A1 | 9/2005 | Adams et al. |
| 2005/0277852 | A1 | 12/2005 | Shih et al. |
| 2005/0287680 | A1 | 12/2005 | Venkatasubbarao et al. |
| 2006/0053870 | A1 | 3/2006 | Berndt |
| 2006/0217893 | A1 | 9/2006 | Li et al. |
| 2006/0223691 | A1 | 10/2006 | Shih et al. |
| 2006/0228657 | A1 | 10/2006 | Masters et al. |
| 2006/0257286 | A1 | 11/2006 | Adams |
| 2007/0089515 | A1 | 4/2007 | Shih et al. |
| 2007/0141721 | A1 | 6/2007 | Vafai et al. |
| 2007/0169553 | A1 | 7/2007 | Mutharasan |
| 2007/0218534 | A1 | 9/2007 | Klenerman et al. |
| 2008/0034840 | A1 | 2/2008 | Mutharasan |
| 2008/0035180 | A1 | 2/2008 | Mutharasan |
| 2009/0007645 | A1 | 1/2009 | Shih et al. |
| 2009/0053709 | A1 | 2/2009 | Mutharasan |
| 2009/0078023 | A1 | 3/2009 | Mutharasan |
| 2009/0203000 | A1 | 8/2009 | Mutharasan |
| 2010/0068697 | A1 | 3/2010 | Shih et al. |
| 2010/0224818 | A1 | 9/2010 | Shih et al. |
| 2010/0239463 | A1 | 9/2010 | Shih et al. |

FOREIGN PATENT DOCUMENTS

| | | |
|---|---|---|
| JP | 3093849 B2 | 4/2000 |
| JP | 2003-298131 A | 10/2003 |
| JP | 2004-265899 A | 9/2004 |
| JP | 2007-67125 A | 3/2007 |
| WO | 98/50773 A2 | 11/1998 |
| WO | 2004/061991 A1 | 7/2004 |
| WO | 2005/043126 A2 | 5/2005 |
| WO | 2006/031072 A1 | 3/2006 |
| WO | 2007/087328 A2 | 8/2007 |
| WO | WO 2007/109228 A1 | 9/2007 |
| WO | 2007/133619 A1 | 11/2007 |
| WO | 2008/020903 A2 | 2/2008 |
| WO | 2008/021187 A2 | 2/2008 |
| WO | 2008/021189 A2 | 2/2008 |
| WO | 2008/101199 A1 | 8/2008 |
| WO | 2009/014830 A1 | 1/2009 |
| WO | 2009/035732 A2 | 3/2009 |
| WO | 2009/035732 A3 | 3/2009 |
| WO | 2009/046251 A2 | 4/2009 |

OTHER PUBLICATIONS

Ammari, H. et al., "T-Scan Electrical Impedance Imaging System for Anomaly Detection", Siam J. Appl. Math., 65(1): 252-266 (2004).

Baselt, D. R. et al., "Biosensor based on force microscope technology", J. Vac. Sci. Technol. B, 14(2): 789-793 (1996).

Birnie, III, D. P. et al., "Coating uniformity and device applicability of spin coated sol-gel PXT films", Microelectronic Engineering, 29: 189-192 (1995).

Bondoux, C. et al., "MgO insulating films prepared by sol-gel route for SiC substrate", J. Europe. Ceramic Soc., 25: 2795-2798 (2005).

Brito, R. et al., "Adsorption of 3-mercaptopropyltrimethoxysilane and 3-aminopropyltrimethoxysilane at platinum electrodes", J. Electroanalytical Chem., 520: 47-52 (2002).

Campbell, G.A., et al., "Piezoelectric excited millimeter-sized cantilever (PEMC) sensor detects *Escherichia coli* O157:H7 in two-hour incubated samples at 4 CFU per gram of beef," J. of Rapid Methods and Automation in Mirobiology, 1-39.

Campbell, G.A., et al., "Detection and quantification of proteins using self-excited PZT-glass millimeter-sized cantilever," Biosensors and Bioelectronics, 26-36, 2005.

Campbell, G.A., "Piezoelectric-excited millimeter-sized cantilever (PEMC) sensors detect *Bacillus anthracis* at 300 spores/mL," Biosensors and Bioelectronics, 37-45, 2005.

Campbell, G.A., et al., "Kinetics of *Bacillus anthracis* spore binding to antibody functionalized PEMC sensors in presence of *Bacillus thuringiensis* and *Bacillus cereus*," J. Publications, Am. Chem. Soc. 25 pages, 2006.

Campbell, G.A., et al., "*Escherichia coli* O157:H7 detection limit of millimeter-sized PZT cantilever sensors in 700 cells/mL," Analytical Sci., 11-13, 2005.

Campbell, G.A., et al., "Detection of pathogen *Escherichia coli* O157:H7 using self-excited PZT-glass microcantilevers," Biosensors and Boelectronics, 14-25, 2005.

Campbell, G.A., "Detection of *Staphylococcus* enterotoxin B at pictogram levels using piezoelectric-excited millimeter-sized cantilever sensors," Submitted on line to J. of Analytical Chem., 1-24, 2006.

Campbell, G.A., et al., "Detect *Escherichia coli* O157:H7 in ground beef samples using piezoelectric excited millimeter-sized cantilever (PEMC) sensors," Submitted on-line to Biosensors and Bioelectronics, 2-34, 2007.

Campbell, G.A., et al., "A method for measuring *Escherichia coli* O157:H7 at 1 cell/mL in 1 liter sample using antibody functional piezoelectric-excited millimeter sized cantilever sensor," Paper submitted on-line to J. of Analytical Chemistry. 1-23, 2007.

Capobianco, J. A., et al., "Methyltrimethoxysilane-insulated piezoelectric microcantilevers for direct, all-electrical biodetection in buffered aqueous solutions", Rev. Sci. Instrum., 77: 125105-1-125105-6 (2006).

(56) References Cited

OTHER PUBLICATIONS

Capobianco, J. A., et al., "3-mercaptopropyltrimethoxysilane as insulating coating and surface for protein immobilization for piezoelectric microcantilever sensors", Rev. Sci. Instrum., 78: 046106-1-046106-3 (2007).
Carlier, S. G., et al., "Elastography", J. Cardiovasc Risk, 9(5): 237-245 (2002).
Carr, D.W., et al., "Fabrication of nanoelectromechanical systems in single crystal silicon using silicon on insulator substrates and electron beam lithography," J. Vac. Sci. Technology, B, 5(6), 2760-2763, 1997.
Che, G. et al., "Molecular recognition based on (3-mercaptopropyl) trimethoxysilane modified gold electrodes", J. Electroanalytical Chem., 417: 155-161 (1996).
Chen, G. Y. et al., "Adsorption-induced surface stress and its effects on resonance frequency of microcantilevers", J. Appl. Phys., 77(8): 3618-3622 (1995).
Chen, X. et al., "Electrochemical and Spectroscopic Characterization of Surface Sol-Gel Processes", Langmuir, 20 (20): 8762-8767 (2004).
Cho, S. H. et al., "Micro-scale metallization on flexible polyimide substrate by Cu electroplating using SU-8 photoresist mask", Thin Solid Films, 475: 68-71 (2005).
Duval, F.F.C. et al., "Stable TiO2/Pt electrode structure for lead containing ferroelectric thick films on silicon MEMS structures", Thin Solid Films, 444: 235-240 (2003).
Feili, D. et al., "Encapsulation of organic field effect transistors for flexible biomedical microimplants", Sensors and Actuators, A120: 101-109 (2005).
Ferrini, R. et al., "Screening Mammography for Breast Cancer: American College of Preventive Medicine Practice Policy Statement", www.acpm.org/breast, pp. 1-4 (2005).
Fritz, J. et al., "Translating Biomolecular Recognition into Nanomechanics", Science, 288: 316-318 (2000).
Fung, Y. S. et al., "Self-Assembled Monolayers as the Coating in a Quartz Piezoelectric Crystal Immunosensor To Detect *Salmonella* in Aqueous Solution", Anal. Chem., 73: 5302-5309 (2001).
Gao, L. et al., "Imaging of the elastic properties of tissue: A review", Ultrasound in Med. & Biol., 22(8): 959-977 (1996). Abstract Only.
Greenleaf, J. F. et al., "Selected Methods for Imaging Elastic Properties of Biological Tissues", Annu. Rev. Biomed. Eng., 5: 57-78 (2003).
Gu, H. et al., "Single-Calcination Synthesis of Pyrochlore-Free 0.9Pb(Mg1/3Nb2/3)O3-0.1PbTiO3 and Pb (Mg1/3Nb2/3)O3 Ceramics Using a Coating Method", J. Am. Ceram. Soc., 86(2): 217-221 (2003).
Haccart, T. et al., "Evaluation of niobium effects on the longitudinal piezoelectric coeffecients of Pb(Zr,Ti)O3 thin films", Appl. Phys. Lett., 76(22): 3292-3294 (2000).
Han, W. et al., "A magnetically driven oscillating probe microscope for operations in liquids", Appl. Phys. Lett., 69(26): 4111-4113 (1996).
Hiboux, S. et al., "Mixed titania-lead oxide seed layers for PZT growth on Pt(111): a study on nucleation, texture and properties", J. Europe. Ceram. Soc., 24: 1593-1596 (2004).
Hwang, I.H. et al., "Self-actuating biosensor using a piezoelectric cantilever and its optimization", Journal of Physics: Conference Series 34, pp. 362-367, 2006.
Hwang, K.S. et al., "In-situ quantitative analysis of a prostate-specific antigen (PSA) using a nanomechanical PZT cantilever", Lab Chip, 4: 547-552 (2004).
Ilic, B. et al., "Mechanical resonant immunospecific biological detector", Appl. Phys. Lett., 77(3): 450-452 (2000).
Itoh, T. et al., "Self-excited force-sensing microcantilevers with piezoelectric thin films for dynamic scanning force microscopy", Sensor and Actuators, A54:477-481 (1996).
Jung, S.K. et al., "Polymeric Mercaptosilane-Modified Platinum Electrodes for Elimination of Interferants in Glucose Biosensors", Anal. Chem., 68: 591-596 (1996).

Kanda, T. et al., "A flat type touch probe sensor using PZT thin film vibrator:", Sensors and Actuators, 83: 67-75 (2000).
Katiyar, P. et al. "Electrical properties of amorphous aluminum oxide thin films", Acta Materialia, 53: 2617-2622 (2005).
Keller, A. et al., "Reliability of Computed Tomography Measurements of Paraspinal Muscle Cross-Sectional Area and Density in Patients With Chronic Low Back Pain", Spine, 28(13): 1455-1460 (2003).
Kelly, J. et al., "Effect of Composition on the Electromechanical Properties of (1–x)Pb(Mg1/3Nb2/3)O3-xPbTiO3 Ceramics" J. Am. Ceram. Soc., 80(4): 957-964 (1997).
Khabari, A. et al., "Partially ionized beam deposition of parylene" J. Non-Crystalline Solids, 351: 3536-3541 (2005).
Kim, S.H. et al., "Influence of Al2O3 diffusion barrier and PbTiO3 seed layer on microstructural and ferroelectric charachteristics of PZT thin films by sol-gel spin coating method," Thin Solid Films, 305: 321-326 (1997).
Kim, S.J. et al., "Fabrication and Characterization of Pb(Zr,Ti)O3 Microcantilever for Resonance Sensors," Jpn. J. Appl. Phys., 42(3): 1475-1478 (2003).
Klissurska, R.D. et al. "Microstructure of PZT sol-gel films on Pt substrates with different adhesion layers," Microelectronic Engineering, 29: 297-300 (1995).
Kruse, S.A. et al., "Tissue characterization using magnetic resonance elastography: preliminary results," Phys. Med. Biol., 45: 1579-1590 (2000).
Kumar, V. et al., "A Simple System for the Preparation of Submicrometer Lead Titanate Powders by the Sol-Gel Method," J. Am. Ceram. Soc., 79(10): 2775-2778 (1996).
Kwok, CLK. et al., "Low temperature perovskite formation of lead zirconate titanate thin films by a seeding process," J. Mater. Res., 8(2): 339-344 (1993).
H. Zhang, et al., "A Sensitive and High-Throughput Assay to Detect Low-Abundance Proteins in Serum," Nature Medicine 12(4) 473-477 (2006).
J. W. Park, S. Kurosawa, H. Aizawa Y. Goda, M. Takai and K. Ishihara, "Piezoelectric Immunosensor for Bisphenol A Based on Signal Enhancing Step With 2-methacrolyloxyethyl Phosphorylcholine Polymeric Nanoparticle," Analyst, 131, 155-162 (2006).
A. M. Smith, G. Ruan, M. N. Rhyner, and S. Nie, "Engineering Luminescent Quantum Dots for In Vivo Molecular and Cellular Imaging," Ann. Biomed. Eng., 34 (1),3-14 (2006).
R. E. Jaeger and L. Egerton, "Hot-Pressing of Potassium-Sodium Niobates," J. Am. Ceram. Soc. 45, 209 (1962).
H. Birol, D. Damjanovic and N. Setter, "Preparation and Characterization of (K0.5Na0.5)NbO3 Ceramics", J. Eur. Ceram. Soc. 26, 861 (2006).
Y. Guo, K. Kakimoto, and H. Ohsato, "Phase Transitional Behavior and Piezoelectric Properties of (Na0.5K0.5)NbO3-LiNbO3 Ceramics," Appl. Phys. Lett., 85, 4121 (2004).
Y. Guo, K. Kakimoto, and H. Ohsato, "(Na0.5K0.5)NbO3-LiTaO3 Lead-free Piezoelectric Ceramics," Mater. Lett., 59, 241 (2005).
H. Li, W. Y. Shih, and W.-H. Shih, "Effect of Antimony Concentration on the Crystalline Structure, Dielectric and Piezoelectric Properties of (Na0.5K0.5)0.945Li0.055Nb1-xSbxO3 Solid Solutions", J. Am. Ceram. Soc., 90, 3070 (2007).
S. Zhang, R. Xia, T. R. Shrout, J. Zang, and J. Wang, "Piezoelectric Properties in Perovskite 0.948(K0.5Na0.5)NbO3-0.052LiSb03 lead-free ceramics", J. App. Phys., 100, 104108 (2006).
X. Li, W. Y. Shih, J. S. Vartuli, D. L. Milius, I. A. Aksay, and W.-H. Shih, "Effect of Transverse Tensile Stress on Electric-Field-Induced Domain Reorientation in Soft PZT: In Situ XRD Study", J. Am. Ceram. Soc. 85 (4), 844 (2002).
Q. Zhu, W. Y. Shih, and W.-H. Shih, "Real-Time, Label-Free, All-Electrical Detection of *Salmonella typhimurium* Using Lead Titanate Zirconate/Gold-Coated Glass Cantilevers at any Relative Humidity," Sensors and Actuators B, 125, 379-388 (2007).
Q. Zhu, W. Y. Shih, and W.-H. Shih, "Length and Thickness Dependence of Longitudinal Flexural Resonance Frequency Shifts of a Piezoelectric Microcantilever Sensor due to Young's Modulus Change," J. Appl. Phys. 104, 074503 (2008).

(56) References Cited

OTHER PUBLICATIONS

Q. Zhu, W.Y. Shih, and W.-H. Shih, "Enhanced Detection Resonance Frequency Shift of a Piezoelectric Microcantilever Sensor by a DC Bias Electric Field in Humidity Detection," Sensors and Actuators, B 138, 1 (2009).
Q. Zhu, W. Y. Shih, and W.-H. Shih, "Mechanism of the Flexural Resonance Frequency Shift of a Piezoelectric Mierocantilever Sensor in a DC Bias Electric Field," *Appl. Phys. Lett.* 92, 033503 (2008).
Q. Zhu, Drexel University (2008).
McGovern, J.P. Drexel University (2008).
Luo, H.Y. Drexel University (2005).
Shin, S., Kim, J.P., Sim, S.J. & Lee, J. A multisized piezoelectric microcantilever biosensor array for the quantitative analysis of mass and surface stress. *Applied Physics Letters* 93,—(2008).
Pang, W. et al. Femtogram mass sensing platform based on lateral extensional mode piezoelectric resonator. *Applied Physics Letters* 88,—(2006).
Cherian, S. & Thundat, T. Determination of adsorption-induced variation in the spring constant of a microcantilever. *Applied Physics Letters* 80, 2219-2221 (2002).
Lee, J.H., Kim, T.S. & Yoon, K.H. Effect of mass and stress on resonant frequency shift of functionalized $Pb(Zr_{0.52}Ti_{0.48})O_3$ thin film microcantilever for the detection of C-reactive protein. *Applied Physics Letters* 84, 3187-3189 (2004).
Lee, J.H. et al. Immunoassay of prostate-specific antigen (PSA) using resonant frequency shift of piezoelectric nanomechanical microcantilever. *Biosensors and Bioelectronics* 20, 2157-2162 (2005).
Shen, Z., Shih, W.Y. & Shih, W.-H. Self-exciting, self-sensing Pb $Zr_{0.53}Ti_{0.47}O_3/SiO_2$ piezoelectric microcantilevers with femtogram/Hertz sensitivity. *Applied Physics Letters* 89, 023506-3 (2006).
Zhu, Q., Shih, W.Y. & Shih, W.-H. In situ, in-liquid, all-electrical detection of *Salmonella typhimurium* using lead titanate zirconate/gold-coated glass cantilevers at any dipping depth. *Biosensors and Bioelectronics* 22, 3132-3138 (2007).
McGovern, J.P. et al. Label-free flow-enhanced specific detection of *Bacillus anthracis* using a piezoelectric microcantilever sensor. *Analyst* 133, 649-654 (2008).
McGovern, J.P., Shih, W.Y. & Shih, W.H. In situ detection of *Bacillus anthracis* spores using fully submersible, self-exciting, self-sensing PMN-PT/Sn piezoelectric microcantilevers. *Analyst* 132, 777-783 (2007).
McGovern, J.-P. et al. Label-free flow-enhanced specific detection of *Bacillus anthracis* using a piezoelectric microcantilever sensor. *The Analyst* 133, 649-654 (2008).
McGovern, J.-P., Shih, W.Y. & Shih, W.-H. In situ detection of *Bacillus anthracis* spores using fully submersible, self-exciting, self-sensing PMN-PT/Sn piezoelectric microcantilevers. *The Analyst* 132, 777-783 (2007).
Zhu, Q., Shih, W.Y. & Shih, W.-H. Mechanism of flexural resonance frequency shift of a piezoelectric microcantilever sensor during humidity detection. *Applied Physics Letters* 92, 183505-3 (2008).
Su, W.-S., Chen, Y.-F., Shih, W.Y., Luo, H. & Shih, W.-H. Domain switching in lead magnesium niobate-lead titanate polycrystalline sheets at single grain level. *Applied Physics Letters* 91, 112903-3 (2007).
Shang, J.K. & Tan, X. Indentation-induced domain switching in Pb(Mgl/3Nb2/3)O3-PbTiO3 crystal. *Acta Materialia* 49, 2993-2999 (2001).
Alguero, M., Jimenez, B. & Pardo, L. Rayleigh type behavior of the Young's modulus of unpoled ferroelectric ceramics and its dependence on temperature. *Applied Physics Letters* 83, 2641-2643 (2003).
Masys, A.J., Ren, W., Yang, G. & Mukherjee, B.K. Piezoelectric strain in lead zirconate titante ceramics as a function of electric field, frequency, and dc bias. *Journal of Applied Physics* 94, 1155-1162 (2003).
Capobianco, J.A., Shih, W.Y., Yuan, Q.-A., Adams, G.P. & Shih, W.-H. Label-free, all-electrical, in situ human epidermal growth receptor 2 detection. *Review of Scientific Instruments* 79, 076101 (2008).

Shih, W.Y., Luo, H., Li, H., Martorano, C. & Shih, W.-H. Sheet geometry enhanced giant piezoelectric coefficients. *Applied Physics Letters* 89, 242913-3 (2006).
Capobianco, J.A., Shih, W.Y. & Shih, W.-H. 3-mercaptopropyltrimethoxysilane as insulating coating and surface for protein immobilization for piezoelectric microcantilever sensors. *Review of Scientific Instruments* 78, 046106 (2007).
Morton, T.A., Myszka, D.G. & Chaiken, I.M. Interpreting Complex Binding-Kinetics from Optical Biosensors—a Comparison of Analysis by Linearization, the Integrated Rate-Equation, and Numerical-Integration. *Analytical Biochemistry* 227, 176-185 (1995).
Shuck, P. & Minton, A.P. Kinetic analysis of biosensor data: elementary test of self-consistency. *Trends Biochemical Sciences* 21, 458-460 (1996).
McKendry, R. et al. Multiple label-free biodetection and quantitative DNA-binding assays on a nanomechanical cantilever array. *Proceedings of the National Academy of Sciences of the United States of America* 99, 9783-9788 (2002).
Ndieyira, J.W. et al. Nanomechanical detection of antibiotic mucopeptide binding in a model for superbug drug resistance. *Nature Nanotechnology* 3, 691-696 (2008).
Sofian M. Kanan and Carl P. Tripp, "An Infrared Study of Adsorbed Organophosphonates on Silica: A Prefiltering Strategy for the Detection of Nerve Agents on Metal Oxide Sensors," Langmuir 2001, 17, 2213-2218, United States of America.
"Enhanced detection resonance frequency shift of a piezoelectric microcantilver sensor by a DC bias electric field in humidity detection," Sensors and Actuators B: Chemical, 2009, vol. 138, United States of America.
J. K. Shang and X. Tan, "Indentation-Induced Domain Switching In Pb(Mg1/3Nb2/3)03-PbTiO3 Crystal" Acta Mater., 2001, pp. 2993-2999, vol. 49, Urbana, Illinois.
IEEE Standard on Piezoelectricity IEEE, New York, 1988, Chap. 6.
L. Bellaiche and David Vanderbilt, Physical Review Letters, 83(7), Aug. 16, 1999, 1347.
S-F. Liu, W. Ren, B. K. Mukherjee, S. J. Zhang, T. R. Shrout, P. W. Rehrig, and W. S. Hackenberger, Appl. Phys. Lett., 83, 2886 (2003).
PZT data, IEEE Micro Electro Mechanical Systems Workshop, Jan.-Feb. 1991, Nara, Japan p. 118.
Xu, et al., "Longtitudinal piezoelectric coefficient measurement for bulk ceramics and thin films using pneumatic pressure rig," Journal of Applied Physics, Jul. 1, 1999, pp. 588-594, vol. 86, No. 1, Pennsylvania.
Li, "Sodium Potassium Niobate-based Lead-free Piezoelectric Ceramics: Bulk and Freestanding Thick Films," Thesis Submitted to Faculty of Drexel University, Jun. 2008, Philadelphia, Pennsylvania.
Li, "Synthesis of Na0.5K0.5NbO3 Piezoelectrics by a Solution Coating Approach," Int. J. Appl. Technol., 2009, pp. 205-215, vol. 6, Issue 2, United States of America.
Hudson, J.B. Surface Science: An Introduction, (Wiley-IEEE, New York, 1998).
Q. Zhu. "Enhanced detection resonance frequency shift of a piezoelectric microcantilever sensor by a DC bias electric field in humidity detection," Sensors and Actuators B: Chemical, 2009, pp. 1-4, vol. 138.
Q. Zhu, W. Y. Shih & W.H. Shih, "Mechanism of flexural resonance frequency shift of a piezoelectric microcantilever sensor during humidity detection," Applied Physics Letters, 2008, vol. 92, United States of America.
Hudson, J.B. Surface Science: An Introduction, Wiley-IEEE, 1998, pp. 96-98, New York.
Leckband, D.E. et al. Force Probe Measurements of Antibody-Antigen Interactions. Methods 20, 329-340 (2000).
O'Sullivan, C.K. & Guilbault, G.G. Commercial quartz crystal microbalances—theory and applications. Biosensors & Bioelectronics 14, 663-670 (1999).
Lofgren, J.A. et al. Comparing ELISA and surface plasmon resonance for assessing clinical immunogenicity of panitumumab. J Immunol 178, 7467-72 (2007).
Borghaei, et al., "Induction of Adaptive Anti-HER2/neu Immune Responses . . . " J. Immunother, Jun. 2007, pp. 455, vol. 30, No. 4.

(56) References Cited

OTHER PUBLICATIONS

H. Yengingil, "Breast Cancer Detection and Differentiation Using Piezoelectric Fingers," PhD Thesis, Drexel University, Philadelphia, PA, Jan. 2009.

E. E. Konofagou, T. Harrigan, and J. Ophir, "Shear Strain Estimation and Lesion Mobility Assessment in Elastography," Ultrasonics, 2000, pp. 400-404, vol. 38.

H.O. Yegingil, W. Y. Shih, W. Anjum, A. D. Brooks and W.-H. Shih, "Soft tissue elastic modulus measurement and tumor detection using piezoelectric fingers," Mat. Res. Soc. Symp. Proc., 2006, vol. 898E.

P. S. Wellman, E. P. Dalton,, D. Krag,, K. A. Kern, R. D. Howe, "Tactile Imaging of Breast Masses: First Clinical Report," Archives of Surgery 136(2), 204-08 (2001).

Z. Shen, W. Y. Shih, and W. -H. Shih, "Mass detection sensitivity of piezoelectric cantilevers with a nonpiezoelectric extension," Rev. Sci. Instrum. 77, 065101 (2006).

A. Markidou, W. Y. Shih, and W.-H. Shih, "Soft-materials elastic and sear moduli measurement using piezoelectric cantilevers," Rev. Sci. Ins. 76, 064302 (2005).

S . T. Szewczyk, W.Y. Shih, and W.-H. Shih, "Palpationlike soft-material elastic modulus measurement using piezoelectric cantilievers," Rev. Sci. Ins., 77, 044302 (2006).

H. O. Yegingil, W. Y. Shih, and W.-H. Shih, "All-electrical indentation shear modulus and elastic modulus measurement using a piezoelectric cantilever with a tip," J. Appl. Phys., 101, 054510 (2007).

W. Jiang and W. Cao, "Intrinsic and coupling-induced elastic nonlinearity of lanthanum-doped lead magnesium niobate-lead titanate electrostrictive ceramic," Appl. Phys. Lett., 77,1387 (2000).

A. W. McFarland, et al., "Influence of surface stress on the resonance behavior of microcantilevers," Appl. Phys. Lett. 87, 053505 (2005).

O. Kwon, "T-scan Electrical Impedance Imaging system for anomaly detection," Siam J. Appl. Math., 2004, pp. 252-266, vol. 65, No. 1.

Sure Touch Exam [online] retrieved Nov. 29, 2010 from the internet @ http://www.medicaltactile.com/default.htm.

Q. Ren and Y. P. Zhao, "Influence of surface stress on frequency of microcantilever-based biosensors," Microsystem Technologies, 2004, pp. 307-314, vol. 10.

E. Chen, "Ultrasound Tissue Displacement and Tissue Elasticity Imaging," Ph.D. dissertation, University of Illinois at Urbana-Champaign, (1995).

Haun, M.J. "Thermodynamic Theory of the Lead Zirconate-Titanate Solid Solution System," The Pennsylvania State University (1988).

Wellman, P. S. et al., "Tactile Imaging: A Method for Documenting Breast Lumps".

Weng, L. et al., "Effect of acetylacetone on the preparation of PZT materials in sol/gel processing", Mater. Sci. Engin., B96: 307-312 (2002).

Wilson, L S et al., "Elastography—the movement begins", Phys. Med. Biol., 45: 1409-1421 (2000).

Wilson, L., et al., "Pezoelectric-excited millimeter-sized cantilever (PEMC) sensor provides viscosity and density measurements," Submitted to Review of Scientific Instruments, 1-26.

Yi, J. W. et al., "Effect of length, width, and mode on the mass detection sensitivity of piezoelectric unimorph cantilevers", J. Appl. Phys., 91(3): 1680-1686 (2002).

Yi, J. W. et al., "In situ cell detection using piezoelectric lead zirconate titanate-stainless steel cantilevers", J. Appl. Phys., 93(1): 619-625 (2003).

Zhao, Q. et al., "Array adsorbent-coated lead zirconate titanate (PZT)/stainless steel cantilevers for dimethyl methyiphosphonate (DMMP) detection", Sensors and Actuators, B117(1): 74-79 (2006). Abstract Only.

Zhou, J. et al., "Zeolite-modified microcantilever gas sensor for indoor air quality control," Sensors and Actuators B, Oct. 1, 2003, 94(3), 337-342.

Zhu, D.M. et al., "Thermal conductivity and electromechanical property of single-crystal lead magnesium niobate titanate", Appl. Phys. Lett., 75(24): 3868-3870 (1999).

Data of Commercially Available Product, EDO Corporation: 1-8 (1999).

Data of Commercially Available Product, APC International, Ltd.: 1-2 (2005).

Campbell, G.A., et al., "Use of Piezoelectric-Excited millimeter Sized Cantilever Sensors to Measure Albumin Interaction with Self-Assembled Monolayers of Alkanethiols Having Different Functional Headgroups," Anal. Chem. 78, 2328-2334 (2006).

Campbell, G.A., et al., "Method of measuring *Bacillus anthracis* spores in the Presence of copious amounts of *Bacillus thurigiensis* and *Bacillus cereus*," Anal. Chem. 79, 1145-1152 (2007).

Campbell, G.A., et al., "PEMC sensor's mass change sensitivity is 20 pg/Hz under liquid immersion," Biosensors and Bioelectronics, 22, 35-41 (2006).
Campbell, G.A., et al., "Detection of *Bacillus anthracis* spores and a model protein usings PEMC sensors in a flow cell at 1 mL/min," Biosensors and Bioelectronics, 22, 78-85 (2006).
Campbell, G.A., et al., "Detection of airborne *Bacillus anthracis* spores by an integrated system of an air sampler and a cantilever immunosensor," Sensors and Actuators B 127, 376-382 (2007).
Maraldo, et al., "Method for Label-Free Detection of Femtogram Quantities of Biologics in Flowing Liquid Samples," Anal. Chem. 79, 2762-2770 (2007).
Maraldo, et al., "Detection and confirmation of *Staphylococcal* enterotoxin B in apple juice and milk using piezoelectric-excited millimeter-sized cantilever sensors at 2.5 fg/mL," Anal Chem. 79, 7636-7643 (2007).
Maraldo, et al., "Method for Quantification of a Prostate Cancer Biomarker in Urine without Sample Preparation," Anal. Chem. 79, 7683-7690 (2007).
Maraldo, et al., "10-Minute assay for detecting *Escherichia coli* O157:H7 in ground beef samples using piezoelectric-excited millimeter-size cantilever sensors." Journal of Food Protection, vol. 70, No. 7, 1670-1677 (2007).
Maraldo, et al., "Preapration-Free Method for Detecting *Escherichia coli* O157:H7 in the Presence of Spinach, Spring Lettuce Mix, and Ground Beef Particulates," Journal of Food Protection, vol. 70, No. 11, 2651-2655 (2007).
Rijal, et al., "PEMC-based method of measuring DNA hybridization at femtomolar concentration directly in human serum and in the presence of copious noncomplementary strands," Anal. Chem., 79, 7392-7400 (2007).
Rijal, et al., "Method for measuring the Self-Assembly of Alkanethiols on Gold at Femtomolar Concentrations," Langmuir, 23, 6856-6863 (2007).
Wilson, et al., "Viscosity and density values from excitation level response of piezoelectric-excited cantilever sensors," Sensors and Actuators A 138, 44-51 (2007).
Gu, et al., "Single-Calcination Synthesis of Pyrochlore-Free 0.9Pb (Mg1/3Nb;2/3)O3-0.1PbTiO3 and Pb(Mg1/3Nb2/3) O3 Ceramics using a Coating Method," J. Am. Ceram. Soc., 86 [2] 217-21 (2003).
Thaysen, et al., "Cantilever-Based Bio-Chemical Sensor Integrated in a Microliquid Handling System," 401-404 (2001).
Li, et al., Micromachined Biomimetic Sensor Using a Modular Artificial Hair Cells, pp. 1-3.
Thaysen, "Label free Detection, BioMEMs Materials and Fabrication Methods," Track 2, 3:00pm, pp. 1-3, Sep. 7, 2002.
Lee, C. et al., "Sol-gel derived PZT force sensor for scanning force microscopy", Mater. Chem. Phys., 44: 25-29 (1996).
Lee, C. et al., "Self-excited piezoelectric PZT microcantilevers for dynamic SFM—with inherent sensing and actuating capabilities", Sensors and Actuators, A72: 179-188 (1999).
Lee, J. H. et al., "Label free novel electrical detection using micromachined PZT monolithic thin film cantilever for the detection of C-reactive protein", Biosensors and Bioelectronics, 20: 269-275 (2004).
Lee, J. H. et al., "Effect of mass and stress on resonant frequency shift of functionalized Pb(Zr0.52Ti0.48)O3 thin film microcantilever for the detection of C-reactive protein", Appl. Phys. Lett., 84(16): 3187-3189 (2004).
Lee, J. H. et al., "Immunnoassay of prostate-specific antigen (PSA) using resonant frequency shift of piezoelectric nanomechanical microcantilever", Biosensors and Bioelectronics, 20: 2157-2162 (2005).

(56) References Cited

OTHER PUBLICATIONS

Lee, S. S. et al., "Self-Excited Piezoelectric Cantilever Oscillators", The 8th International Conference on Solid-State Sensors and Actuators, and Eurosensors IX, Stockholm, Sweden: 417-420 (1995).
Lee, Y. et al., "A Piezoelectric Micro-Cantilever Bio-Sensor Using the Mass-Microbalancing Technique With Self-Excitation", The 13th International Conference on Solid-State Sensors, Actuators, and Microsystems, Seoul, Korea: 644-647 (2005).
Li, S. et al., "The intrinsic nature of nonlinear behavior observed in lead zirconate titanate ferroelectric ceramic", J. Appl. Phys., 69(10): 7219-7224 (1991).
Li, X. et al., "Detection of water-ice transition using a lead zirconate titanate/brass transducer", J. Appl. Phys., 92(1): 106-111 (2002).
Lin, Z. et al., "Operation of an Ultrasensitive 30-MHz Quartz Crystal Microbalance in Liquids", Anal. Chem., 65(11): 1546-1551 (1993).
Liu, W. et al., "Preparation and orientation control of Pb1.1(Zr0.3Ti0.7)O3 thin films by a modified sol-gel process", Mat. Lett., 46: 239-243 (2000).
Luo, H. et al., "Synthesis of PMN and 65PMN-35PT Ceramics and Films by a New Suspension Method", Perovskite, Piezoelectric, and Dielectric Ceramics: 251-260.
Luo, H. et al., "Comparison in the Coating of Mg(OH)2 on Micron-Sized and Nanometer-Sized Nb2O5 Particles", Int. J. Appl. Ceram. Technol., 1(2): 146-154 (2004).
Luo, H., "Colloidal Processing of PMN-PT Thick Films for Piezoelectric Sensor Applications", A Thesis Submitted to the Faculty of Drexel University in Jun. of 2005.
Maki, K. et al., "Evaluation of Pb(Kr,Ti)O3 Films Derived from Propylene-Glycol-Based Sol-Gel Solutions", Jpn. J. Appl. Phys., 39(9B): 5421-5425 (2000).
Maraldo, D. et al., "Resonant-mode millimeter sized cantilever biosensor for continuous detection of proteins and pathogens in flowing liquids," Dept. of Chem. and Biological Eng., 1-21.
Matsui, Y. et al., "Highly Oxidation-Resistant TiN Barrier Layers for Ferroelectric Capacitors", Jpn. J. Appl. Phys., 36 (3B): 1586-1588 (1997).
Mazza, E. et al., Biomechanics, http://www.zfm.ethz.ch/e/res/bio/, 1-10.
McGovern, J.P. et al., "Real-Time *Salmonella* Detection Using Lead Zirconate Titanate-Titanium Microcantilevers", Mater. Res. Soc. Symp. Proc., 845: AA3.8.1-AA3.8.6 (2005).
Mueller, V. et al., "Nonlinearity and scaling behavior in donor-doped lead zirconate titanate piezoceramic", Appl. Phys. Lett., 72(21): 2692-2694 (1998).
Mulvihill, M. L. et al., "The Role of Processing Variables in the Flux Growth of Lead Zinc Niobate-Lead Titanate Relaxor Ferroelectric Single Crystals", Jpn. J. Appl. Phys., 35(7): 3984-3990 (1996).
Niedziolka, J. et al., "Charaterisation of gold electrodes modified with methyltrimethoxysilane and (3-mercaptopropyl)trimethoxysilane sol-gel processed films", J. Electroanalytical Chem., 578: 239-245 (2005).
Nguyen, L. T. T. et al., "Synthesis and characterization of a photosensitive polyimide precursor and its photocuring behavior for lithography applications", Optical Materials, 29: 610-618 (2007).
Oden, P. I. et al., "Viscous drag measurements utilizing microfabricated cantilevers", Appl. Phys. Lett., 68(26): 3814-3816 (1996).
Ohnmacht, M. et al., "Microcoils and microrelays—an optimized multilayer fabrication process", Sensors and Actuators, 83: 124-129 (2000).
Park, G.T. et al., "Measurement of piezoelectric coefficients of lead zirconate titanate thin films by strain-monitoring pneumatic loading method", Appl. Phys. Lett., 80(24): 4606-4608 (2002).
Park, S.E. et al., "Ultrahigh strain and piezoelectric behavior in relaxor based ferroelectric single crystals", J. Appl. Phys., 82(4): 1804-1811 (1997).
Piezo Systems, Inc., "Piezoceraminc Sheets and Their Properties", Piezo Systems, Inc. Catalog: 1-3 (2007).
Pons, T. et al., "Solution-phase single quantum dot fluorescence resonance energy transfer", J. Amer. Chem. Soc., 128(47): 15324-15331 (2006). Abstract Only.
Ren, W. et al., "Non linear strain and DC bias induced piezoelectric behaviour of electrostrictive lead magnesium niobate-lead titanate ceramics under high electric fields", J. Phys. D: Appl. Phys., 35: 1550-1554 (2002).
Ren, W. et al., "Nonlinear behavior of piezoelectric lead zinc niobate-lead titanate single crystals under ac electric fields and dc bias", Appl. Phys. Lett., 83(25): 5268-5270 (2003).
Rosenberg, RD et al., "Effects of age, breast density, ethnicity and estrogen replacement therapy on screening mammographic sensitivity and cancer stage at diagnosis: review of 183,134 screening mammograms in Albuquerque, New Mexico", Radiology, 209(2): 511-5118 (1998). Abstract Only.
Saito, Y. et al., "Lead-free piezoceramics", Nature, 432: 84-87 (2004).
Schemmel, A. et al., "Single molecule force spectrometer with magnetic force control and inductive detection", Rev. Sci. Instrum., 70(2): 1313-1317 (1999).
Shen, Z. et al., "Microfabrication of Miniaturized PZT/SiO2 Piezoelectric Microcantilever for Rapid, Direct, In-situ Biosensing", MRS Fall Meeting, Boston: 1-23 (2005).
Shen, Z. et al., "Self-exciting, self-sensing PbZr0.53Ti0.47O3/SiO2 piezoelectric microcantilevers with femtogram/Hertz sensitivity", Appl. Phys. Lett., 89: 023506-1-023506-3 (2006).
Shih, W. et al., "Simultaneous liquid viscosity and density determination with piezoelectric unimorph cantilevers", J. Appl. Phys., 89(2): 1497-1505 (2001).
Shih, W. et al., "Ultrasensitive Pathogen Quantification in Drinking Water Using Highly Piezoelectric Microcantilevers", Amer. Chem. Soc., Chapter 23, 179-185 (2005).
Shih, W. et al., "Nanosensors for Environmental Applications", Nanotechnologies for the Life Sciences, 5: 271-293 (2005).
Straub, V. et al., "Contrast Agent-Enhanced Magnetic Resonance Imaging of Skeletal Muscle Damage in Animal Models of Muscular Dystrophy", Magn. Reson. Med., 44: 655-659 (2000).
Thompson, W. R. et al., "Hydrolysis and Condensation of Self-Assembled Monolayers of (3-Mercaptopropyl) trimethoxysilane on Ag and Au Surfaces", Langmuir, 13: 2291-2302 (1997).
Thundat, T. et al., "Detection of mercury vapor using resonating microcantilevers", Appl. Phys. Lett., 66(13): 1695-1697 (1995).
Tslonsky, M. et al., "Sol-Gel-Derived Ceramic-Carbon Composite Electrodes: Introduction and Scope of Applications", Anal. Chem., 66: 1747-1753 (1994).
Tu, Y. L. et al., "A study of the effects of process variables on the properties of PZT films produced by a single-layer sol-gel technique", J. Mater. Sci., 30: 2507-2516 (1995).
Udayakumar, K. R. et al., "Thickness-dependent electrical characteristics of lead zirconate titanate thin films", J. Appl. Phys., 77(8): 3981-3986 (1995).
Wang, Q.M. et al., "Nonlinear piezoelectric behavior of ceramic bending mode actuators under strong electric fields", J. Appl. Phys., 86(6): 3352-3360 (1999).
Wang, Y. et al., "Tactile Mapping of Palpable Abnormalities for Breast Cancer Diagnosis".
Ward, M. D. et al., "In Situ Interfacial Mass Detection with Piezoelectric Transducers", Science, 249: 1000-1007 (1990).
Wellman, P. S. et al., "Breast Tissue Stiffness in Compression is Correlated to Histological Diagnosis", http://biorobotics.harvard.edu/pubs/mechprops: 1-15.
Wellman, P. S. et al., "Tactile Imaging of Breast Masses", Arch. Surg., 136: 204-208 (2001).

* cited by examiner

Figure 8
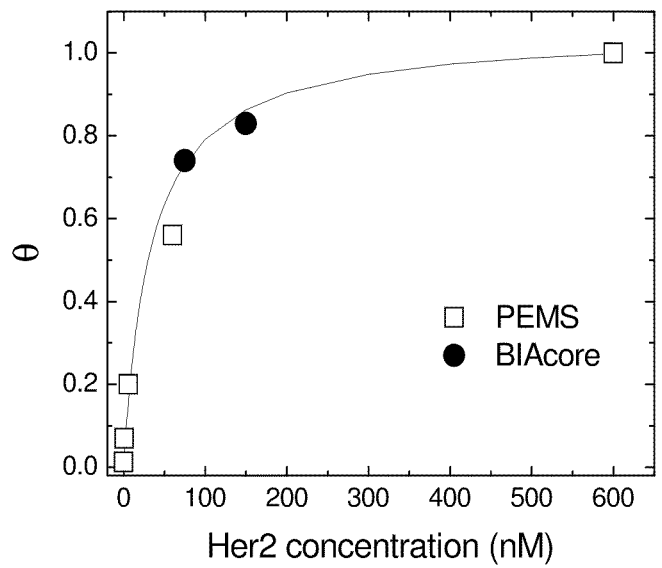
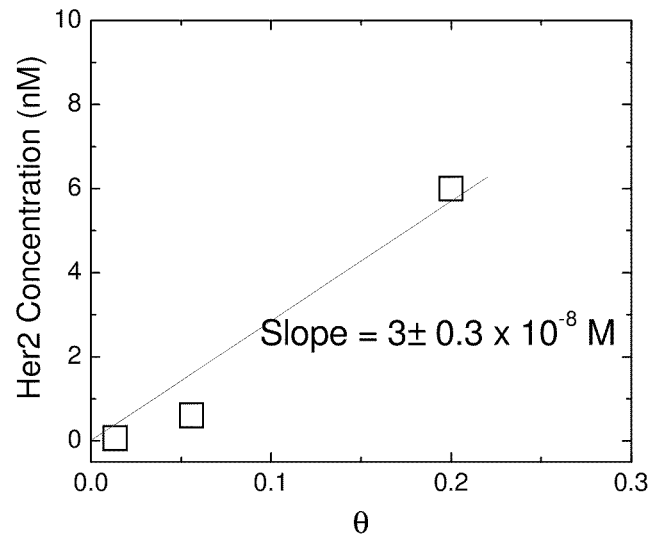
Figure 9

Figure 10
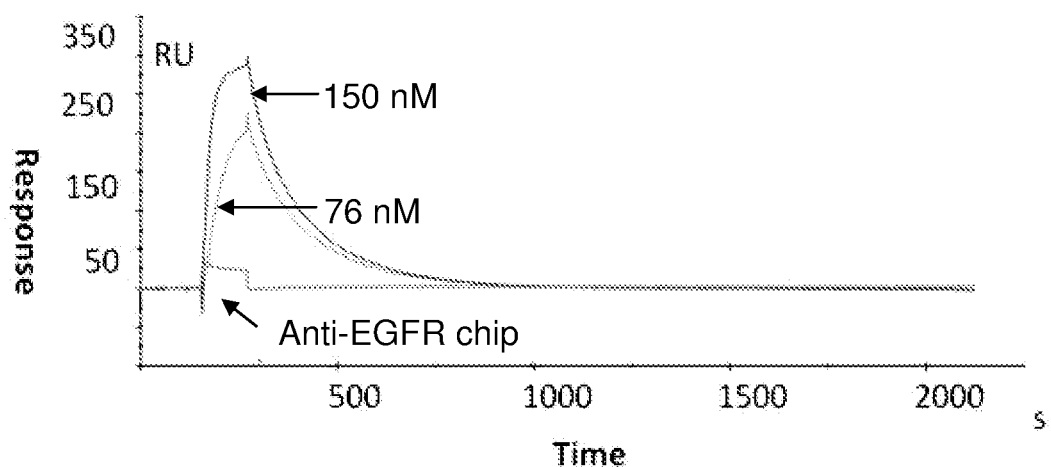
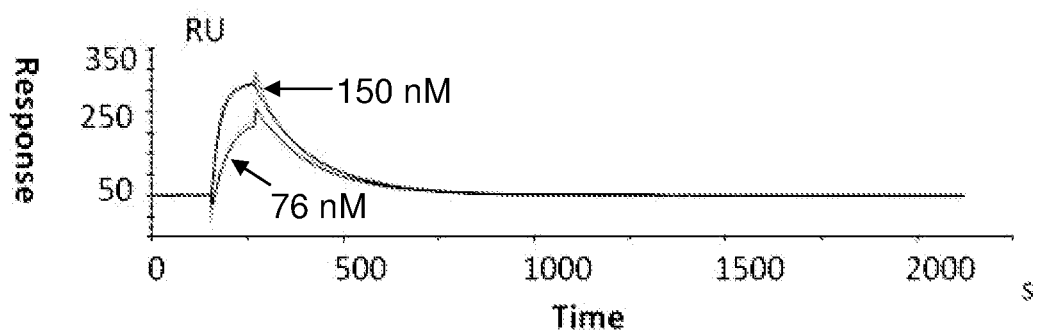
Figure 11

DETERMINATION OF DISSOCIATION CONSTANTS USING PIEZOELECTRIC MICROCANTILEVERS

CROSS REFERENCE TO RELATED APPLICATIONS

This application claims the benefit of U.S. Provisional Application No. 61/249,924, filed Oct. 8, 2009, the entirety of which is incorporated herein.

STATEMENT OF GOVERNMENT INTEREST

This invention was reduced to practice with Government support under Grant No. RO1 EB000720 awarded by the National Institutes of Health; the Government is therefore entitled to certain rights to this invention. This work was also supported by the Nanotechnology Institute (NTI) of southeastern Pennsylvania.

BACKGROUND OF THE INVENTION

1. Field of the Invention

The invention relates to methods for determining dissociation constants.

2. Description of the Related Technology

Proteins are vital parts of living organisms, as they are the main components of the physiological metabolic pathways of cells. Quantification of protein-protein and protein-mRNA interactions is an important step towards understanding the physiological metabolic pathways. A key parameter that characterizes the strength of any protein-protein or protein-mRNA interaction is the equilibrium dissociation constant, $K_d$ (in units of molar (M)) between the two molecules. Traditionally, $K_d$ is measured using equilibrium dialysis through a semipermeable membrane, which is tedious and time consuming.

Alternatively, one can use a surface plasma resonance (SPR) instrument, such as the optical sensor offered by Biacore, to measure $K_d$. However, such optical sensors are expensive and many laboratories do not have access to an optical sensor capable of SPR.

In this disclosure, we show that the dissociation constant, $K_d$, between two molecules can be easily and accurately measured using piezoelectric microcantilever sensors (PEMS). The advantage of the PEMS methodology is low-cost. In addition, the PEMS measurement is rapid and label-free.

U.S. Pat. No. 2006/0065046 (Battiston) suggests a method for measuring binding constants, association or dissociation constants by measuring a piezoelectric microcantilever deflection in a stagnant body of analyte liquid and measuring deflection as a function of time for a flowing body of analyte liquid. Battiston, however, fails to provide details regarding how the dissociation constant is calculated.

U.S. Pat. No. 6,033,913 (Morozov) discloses a method for determining ligand interaction with macromolecules, such as proteins. In Example 1, a cantilever sensor was allowed to contact a ligand and glucose solution. Morozov estimated the binding constant from a graph of tension as a function of time for various glucose solution concentrations. By graphing the inverse tension changes of the cantilever sensor as a function of the inverse glucose concentration, Morozov was able to calculate the dissociation constant. Morozov's method, however, does not use a piezoelectric microcantilever.

Piezoelectric microcantilever sensors (PEMS) consisting of a highly piezoelectric layer bonded to a nonpiezoelectric layer are a new type of biosensors whose mechanical resonance can both be excited and detected by electrical means. With receptors immobilized on the PEMS surface, binding of antigens shifts PEMS resonance frequency. Real-time, label-free antigen detection is achieved by electrically monitoring the PEMS resonance frequency shift. J. W. Yi, W. Y. Shih, and W. H. Shih, "Effect of length, width, and mode on the mass detection sensitivity of piezoelectric unimorph cantilevers," *J. Appl. Phys.* 91 (3), 1680 (2002). PEMS detection sensitivity is strongly related to the thickness and the size of the PEMS. Generally, a PEMS detection sensitivity increases with a reduced PEMS size and thickness. For example, a lead zirconate titanate (PZT)/glass PEMS about 1 mm long consisting of a 127 μm commercial PZT layer on a 75-150 μm glass layer with a 2 mm long glass tip generally exhibited a mass detection sensitivity on the order of $10^{-10}$ g/Hz. Q. Zhu, W. Y. Shih, and W.-H. Shih, "Real-Time, Label-Free, All-Electrical Detection of *Salmonella typhimurium* Using Lead Titanate Zirconate/Gold-Coated Glass Cantilevers at any Relative Humidity," *Sensors and Actuators* B, 125, 379-388 (2007), Q. Zhu, W. Y. Shih, and W.-H. Shih, "In-Situ, In-Water Detection of *Salmonella typhimurium* Using Lead Titanate Zirconate/Gold-Coated Glass Cantilevers at any Dipping Depth," *Biosensors and Bioelectronics*, 22, 3132 (2007), J.-P. McGovern, W. Y. Shih, R. Rest, M. Purohit, Y. Pandia, and W.-H. Shih, "Label-Free Flow-Enhanced Specific Detection of *Bacillus anthracis* Detection Using a Piezoelectric Microcantilever Sensor," *The Analyst*, 132, 649-654 (2008), J. Capobianco, W. Y. Shih, and W. H. Shih, "3-Mercaptopropyltrimethoxysilane as Insulating Coating and Surface for Protein Immobilization for Piezoelectric Microcantilever Sensors," *Rev. Sci. Instr.*, 78, 046106 (2007), and J. Capobianco, W. Y. Shih, W.-H. Shih, Q.-A. Yuan, and G. P. Adams, "Label-free, All-electrical, In-Situ Human Epidermal Growth Receptor-2 Detection," *Rev. Sci. Instrum.* 79, 076101 (2008). A lead magnesium niobate-lead titanate, $(PbMg_{1/3}Nb_{2/3}O_3)_{0.63}$—$(PbTiO_3)_{0.37}$ (PMN-PT)/tin PEMS 600-1200 μm long consisting of an 8 μm thick PMN-PT layer bonded with a 5 μm thick tin layer exhibited a mass detection sensitivity on the order of $10^{-12}$-$10^{-13}$ g/Hz. J.-P. McGovern, W. Y. Shih, and W.-H. Shih, "In-Situ Detection of *Bacillus Anthracis* Spores Using Fully Submersible, Self-Exciting, Self-Sensing PMN-PT/Sn Piezoelectric Microcantilevers," *The Analyst*, 132, 777-783 (2007) and a PZT/SiO$_2$ 60 μm long consisting of a 1 μm thick PZT thin film on 1 μm thick SiO$_2$ layer with a 20 μm long SiO$_2$ tip exhibited a mass sensitivity of $10^{-16}$ g/Hz. Z. Shen, W. Y. Shih, and W.-H. Shih, "Self-Exciting, Self-Sensing PZT/SiO$_2$ Piezoelectric Microcantilever Sensors with Femtogram/Hz Sensitivity," *Appl. Phys. Lett.*, 89, 023506 (2006). Due to thickness and size differences, for Her2 detection, with the same single-chain variable fragment (scFv) antibody, H3, immobilized on the PEMS 3-mercaptopropyl-trimethoxysilane (MPS) insulation surface, a 127-μm thick PZT/glass PEMS exhibited only a μg/ml concentration sensitivity while an 8-μm thick PMN-PT PEMS exhibited a much lower, clinically relevant 5 ng/ml concentration sensitivity, both in a background of 1 mg/ml of bovine serum albumin (BSA) using lower-frequency flexural modes.

As shown by more recent studies, Q. Zhu, W. Y. Shih, and W.-H. Shih, "Mechanism of Flexural Resonance Frequency Shift of a Piezoelectric Microcantilever Sensor during Humidity Detection," *Appl. Phys. Lett.* 92, 183505 (2008) and Q. Zhu, W. Y. Shih, and W.-H. Shih, "Length and Thickness Dependence of Longitudinal Flexural Resonance Frequency Shifts of a Piezoelectric Microcantilever Sensor due to Young's Modulus Change," *J. Appl. Phys.* 104, 074503 (2008). PEMS detection resonance frequency shift was primarily due to the elastic modulus change in the piezoelectric layer from the binding-induced surface stress. As a result, the mass sensitivity of a PMN-PT PEMS and that of a PZT PEMS were respectively 300 times and 100 times higher than could be accounted for by mass loading alone. With a DC bias electric field, the mass sensitivity of a PMN-PT PEMS could even be further enhanced to more than 1000 times higher than could be accounted for by mass loading alone. Q. Zhu, W. Y. Shih, and W.-H. Shih, "Enhanced Detection Resonance Frequency Shift of a Piezoelectric Microcantilever Sensor by a DC Bias Electric Field in Humidity Detection," Sensors and Actuators, B 138, 1 (2009). These studies also revealed that due to the presence of the highly piezoelectric layer, PEMS could exhibit high-frequency non-flexural resonance modes such as width, length and thickness extension modes that silicon-based microcantilevers lack. Q. Zhu, W. Y. Shih, and W.-H. Shih, "Mechanism of the Flexural Resonance Frequency Shift of a Piezoelectric Microcantilever Sensor in a DC Bias Electric Field," Appl. Phys. Lett. 92, 033503 (2008).

At the same time, it was also shown that as a result of the elastic modulus change mechanism, a PEMS relative resonance frequency shift, $\Delta f/f$, was directly proportional to the binding-induced surface stress and inversely proportional to the PEMS thickness where $\Delta f$ and f denotes a PEMS resonance frequency shift and resonance frequency, respectively. This suggests that under the same detection conditions, $\Delta f$ could be higher with a high-frequency resonance mode to result in higher detection sensitivity. As non-flexural extension mode resonance occur at a much higher frequency than flexural-mode resonance, detection using non-flexural resonance modes potentially can increase PEMS sensitivity without size reduction.

SUMMARY OF THE INVENTION

The invention is directed to a method for determining the dissociation constant ($K_d$) by plotting resonance frequency shift as a function of time for various target analyte concentrations. From this graph, the fraction of saturation, i.e. equilibrium fraction of bound binding sites out of all available binding sites on the sensor surface may be estimated by taking the ratio of the equilibrium resonance frequency shift at a selected concentration to the saturated equilibrium frequency shift of the sensor at a higher concentration. The dissociation constant is the inverse slope of the line produced by graphing the fraction of saturation as a function of concentration.

BRIEF DESCRIPTION OF THE DRAWINGS

FIG. 8 shows a plot of $\theta$ versus c for the PEMS measurement of Example 2 as squares and the BIAcore measurement of Example 2 as circles.

FIG. 9 shows a plot of c versus $\theta$ for the concentrations of Example 2 below 6 nM where $\theta$ was less than 0.25.

FIG. 10 shows the BIAcore response versus time of the H3-coated chips and anti-EGFR-coated control chips at 150 and 76 nM of Example 2.

FIG. 11 shows the BIAcore response of the H3-coated chips of Example 2 versus time after subtracting the response of anti-EGFR-coated control chips.

DETAILED DESCRIPTION OF THE PREFERRED EMBODIMENTS

For illustrative purposes, the principles of the present invention are described by referencing various exemplary embodiments thereof. Although certain embodiments of the invention are specifically described herein, one of ordinary skill in the art will readily recognize that the same principles are equally applicable to, and can be employed in other apparatuses and methods. Before explaining the disclosed embodiments of the present invention in detail, it is to be understood that the invention is not limited in its application to the details of any particular embodiment shown. The terminology used herein is for the purpose of description and not of limitation. Further, although certain methods are described with reference to certain steps that are presented herein in certain order, in many instances, these steps may be performed in any order as may be appreciated by one skilled in the art, and the methods are not limited to the particular arrangement of steps disclosed herein.

It must be noted that as used herein and in the appended claims, the singular forms "a", "an", and "the" include plural references unless the context clearly dictates otherwise. Thus, for example, reference to "a sensor" includes a plurality of sensors and equivalents thereof known to those skilled in the art, and so forth. As well, the terms "a" (or "an"), "one or more" and "at least one" can be used interchangeably herein.

It is also to be noted that the terms "comprising", "including", and "having" can be used interchangeably.

Piezoelectric microcantilever sensors (PEMS) use an electrical means for detection. Receptors are coated on the surface of PEMS to bind molecules of interest. The PEMS detects a change because newly bound target molecules shift the mechanical resonance frequency of the device. By monitoring the resonance frequency shifts, a PEMS is capable of rapid, label-free, in situ quantitative detection of organic compounds or molecules including pathogens, antigens and proteins in a small volume solution (e.g. 100 μl) or in a cell culture using simple all-electrical measurements. PEMS are capable of electric actuation and detection and may also be constructed as an array for simultaneous monitoring of multiple target compounds or molecules.

Figure 1A:
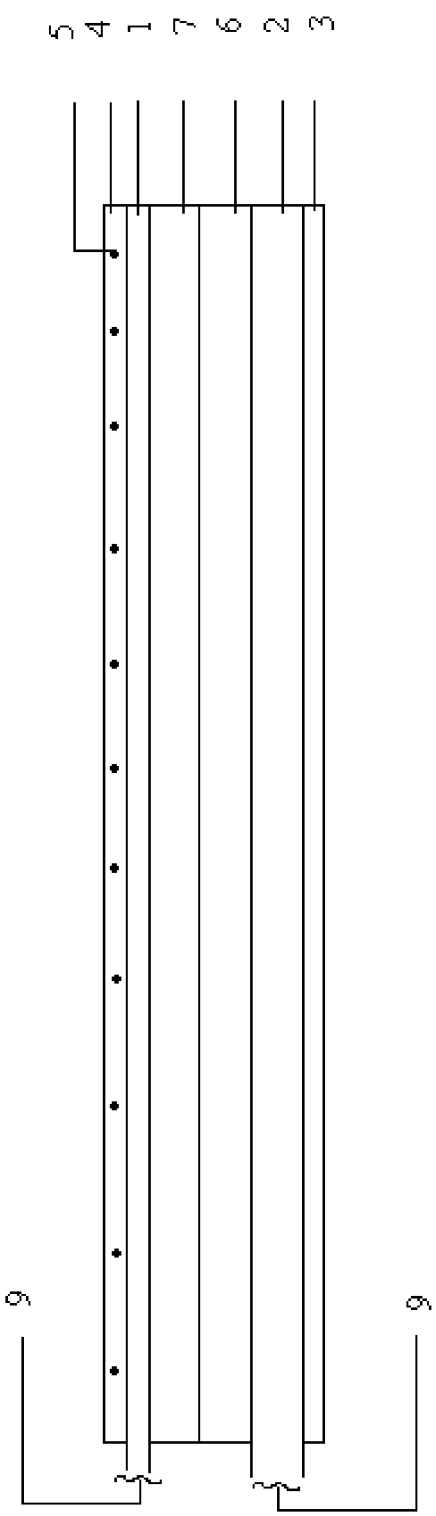
FIG. 1(a) is a cross section of one embodiment of a piezoelectric microcantilever in accordance with the present invention.

FIG. 1(a) shows the basic structure of a microcantilever sensor. A PEMS includes a conductive element 1 and a second conductive element 2 (bottom electrode), electrically insulating layer 3, receptor immobilization layer 4, receptors 5, at least one non-piezoelectric layer 6, and at least one piezoelectric layer 7. The PEMS shown in FIG. 1(a) also includes electrical leads 9.

Conductive elements 1, 2 may be any element capable of conducting an electrical signal from the piezoelectric layer to a device for detecting that signal. In a preferred embodiment, conductive elements 1 and 2 are electrodes which may be constructed from any conductive material. Preferably, the first electrode 1 is constructed from Au/Cr or Pt/Ti and subsequently patterned in several regions. The second electrode 2 is preferably constructed from Pt/$TiO_2$ on $SiO_2$ for PZT/$SiO_2$ PEMS or Pt/Ti on a metal substrate or non-piezoelectric layer and subsequently patterned as well.

In order to maintain functionality in solution by preventing conduction, it may be useful to electrically separate or buffer conductive element 1 and second conductive element 2. Conductive element 1 is patterned slightly smaller than the piezoelectric layer 7 to ensure complete insulation of the edges and corners thereof. Any electrically insulating layer 3 may be used as a coating to achieve electrical separation or buffering.

Alternatively, a PEMS may be insulated using self-assembled monolayers with hydrophobic properties, preferably methyltrimethoxysilane (MTMS) or a combination of MTMS with parylene coatings of varying thicknesses, may also be used. When immersed in a PBS solution, an MTMS insulated piezoelectric microcantilever yields strong resonance peak intensities and prevents background resonance frequency shifts greater than 30 Hz over a period of 30 minutes.

Other insulation materials may include 3-mercaptopropyl trimethoxysilane, $Al_2O_3$, $SiO_2$ and any functional hydrophobic silane, having a hydrophobic group selected from the group consisting of alkyl, phenyl, alkyl halide, alkene, alkyne, and sulfhydryl. In a preferred embodiment, the insulation material is mercaptopropylsilane (MPTS), which can also function to immobilize a receptor on the cantilever. The insulating materials may also include any combination of any of MTMS, MPTS, parylene, 3-mercaptopropyl trimethoxysilane, $Al_2O_3$, $SiO_2$, any functional hydrophobic silane having a hydrophobic group selected from the group consisting of alkyl, phenyl, alkyl halide, alkene, alkyne, and sulfhydryl, or a combination thereof.

Receptors 5 may be densely packed and immobilized onto, for example, a bi-functional linker modified sensor surface. Any receptor, such as specially synthesized cavitants, DNA oligonucleotides, proteins, single chain variable fragments (scFvs), enzymes, and antibodies to cells, antigens, pathogens, viruses, parasites, or combinations thereof may be bound to the sensor surface.

Any means of adhering receptors 5 to the sensor surface may be utilized. In a preferred embodiment, receptors 5 are bound to the electrodes using an immobilization coating 4, such as self assembled monolayers ("SAM"), MPTS and bi-functional linkers. In one embodiment, for purposes of binding scFv, the immobilization coating may be a self assembled monolayer of 3-mercaptoproprionic acid (MPA) on a copper and gold-coated electrode activated with 1-ethyl-3-(3-dimethylaminopropy)carbodimide hydrochloride (EDC) and 5 mg/ml N-hydroxysulfosuccinimide (NHS).

The PEMS also includes at least one non-piezoelectric layer 6, which may be fabricated from any compatible material, including a ceramic material, a polymeric material, a metallic material or combinations thereof. Preferably the non-piezoelectric layer 6 is fabricated from silicon dioxide ($SiO_2$) and silicon nitride ($Si_3N_4$) for PZT-thin film based PEMS. For example, a silicon nitride coating on single crystal silicon wafer may be prepared by low press chemical vapor deposition. A low stress silicon dioxide layer may subsequently be deposited on the silicon nitride layer by growing silicon dioxide films using low temperature oxide deposition or plasma enhanced chemical vapor deposition. For PMN-PT-based PEMS, the non-piezoelectric layer can be any ceramic, metallic, or polymeric layer. A metallic layer such as Cu, tin, Ni, Ti, etc., or any combination is preferred because it can be provided by simple electroplating.

Non-piezoelectric layer 6 may be bonded to a shorter piezoelectric layer 7 so that the portion of non-piezoelectric layer 6 extending beyond the end of piezoelectric layer 7 forms a non-piezoelectric tip. Both piezoelectric layer 7 and non-piezoelectric layer 6 may be attached to a clamp. In an alternative embodiment, piezoelectric layer 7 may extend beyond non-piezoelectric layer 6, forming a piezoelectric tip. Optionally, the PEMS may be constructed so that neither piezoelectric layer 7 nor the non-piezoelectric layer 6 extends beyond the other. In order to achieve the best results, one of the piezoelectric 7 and non-piezoelectric layers 6 preferably extends beyond the other to form a tip. A PEMS may also include multiple piezoelectric and non-piezoelectric layers. For example, a non-piezoelectric layer may be placed between two piezoelectric layers or a piezoelectric layer may be placed between two non-piezoelectric layers.

A significant aspect of the microcantilever device is the fabrication of a highly piezoelectric layer 7, which enables electrical detection and actuation within the cantilever. The piezoelectric layer may function as a driving element, vibrating element and sensing element. Applying an AC voltage (input) across the piezoelectric layer bends and vibrates the PEMS, which in turn induces a piezoelectric voltage that produces readily detectable changes in the magnitude and phase of the output voltage. The resonance frequency of the PEMS is obtained by monitoring the maximum of the phase shift of the output voltage. This measurement is accomplished all-electrically, i.e., electrical actuation and electrical sensing.

Piezoelectric layer 7 may be constructed from any piezoelectric material, including a lead-free piezoelectric material such as $(Na_{0.5}K_{0.5})_{0.945}Li_{0.055}Nb_{0.96}O_3$ (hereinafter "Sb—NKNLN"), Sb—$(Na_{0.5}K_{0.5})NbO_3$—$LiTaO_3$ (hereinafter "Sb—NKNLT"), Sr—$(Na_{0.5}K_{0.5})NbO_3$—$LiTaO_3$ (Sr—NKNLN), Sr—$Na_{0.5}K_{0.5})NbO_3$—$LiTaO_3$ (Sr—NKNLT), SbSr—$(Na_{0.5}K_{0.5})NbO_3$—$LiTaO_3$ (SrSb—NKNLN), SrSb—$Na_{0.5}K_{0.5})NbO_3$—$LiTaO_3$ (SbSr—NKNLT), solid solutions with $(Bi_{0.5}K_{0.5})TiO_3$, $(Bi_{0.5}Na_{0.5})TiO_3$, Ba(Zr$_x$ Ti$_{1-x}$)O$_3$. BaTiO$_3$ (hereinafter "BT"), (Bi$_{1/2}$K$_{1/2}$)TiO$_3$ (hereinafter "BKT"), (Bi$_{1/2}$Na$_{1/2}$)TiO$_3$ (hereinafter "BNT"), Ba(Zr$_x$Ti$_{1-x}$)O$_3$ (hereinafter "BZT"), Bi(Zn$_{1/2}$Ti$_{1/2}$)O$_3$ (hereinafter "BiZT"), (Na$_x$K$_{1-x}$)NbO$_3$ (hereinafter "NKN"), BiScO$_3$—PbTiO$_3$BaTiO$_3$—(Bi$_{1/2}$K$_{1/2}$)TiO$_3$ (hereinafter "BKBT"), (Bi$_{1/2}$Na$_{1/2}$)TiO$_3$—(Bi$_{1/2}$K$_{1/2}$)TiO$_3$ (hereinafter "BNKT"), (Bi$_{1/2}$Na$_{1/2}$)TiO$_3$—BaTiO$_3$ (hereinafter "BNBT"), (Bi$_{1/2}$Na$_{1/2}$)TiO$_3$—Ba(Zr$_x$Ti$_{1-x}$)O$_3$ (hereinafter "BNBZT") and (Bi$_{1/2}$Na$_{1/2}$)TiO$_3$—BaTiO$_3$—(Bi$_{1/2}$K$_{1/2}$)TiO$_3$ (hereinafter "BNBK").

In a preferred embodiment, the piezoelectric layer is fabricated from highly piezoelectric lead magnesium niobate-lead titanate films, e.g. (Pb(Mg$_{1/3}$Nb$_{2/3}$)O$_3$)$_{0.65}$—(PbTiO$_3$)$_{0.35}$ (PMN$_{0.65}$—PT$_{0.35}$) (PMN-PT), highly piezoelectric lead zirconate titanate (PZT) films or high piezoelectric lead-free films. Additionally, piezoelectric layer 7 may be fabricated in any form, preferably having free standing film geometry to enhance domain wall motion and piezoelectric performance. In another embodiment a PEMS may be constructed from highly piezoelectric lead zirconate titanate (PZT).

A PZT/SiO$_2$ piezoelectric layer 7 of film may be formed on silicon wafers and attached to a substrate, such as glass, to form an array. It is also possible to fabricate thin PZT films, of 1.0 to 2.0 µm in thickness, on a variety of different substrates using a sol-gel process.

Suitable methods for fabrication of the piezoelectric microcantilever sensor and flow cells for use with such sensors can be found, for example, in International publication no. WO 2008/067386, the disclosure of which is hereby incorporated by reference herein for the purpose of describing such fabrication methods and flow cells.

When the sensor has one fixed end and one free end a node will always form at the fixed end while an antinode will always form at the free end. The simplest standing wave that can form under these circumstances is one-quarter wavelength long. To make the next possible standing wave, both a node and an antinode are added, dividing the drawing up into thirds. This now gives three-quarters of a wavelength. Repeating this procedure, five-quarters of a wavelength is obtained, then seven-quarters, etc. In this arrangement, there are always an odd number of quarter wavelengths present. Thus the wavelengths of the harmonics are always fractional multiples of the fundamental wavelength with an odd number in the denominator Likewise, the frequencies of the harmonics are always odd multiples of the fundamental frequency. FIG. 1(d) depicts the waves that satisfy the boundary conditions for length mode extension vibrations. Therefore as a result of the boundary conditions, the equation that can be used to predict the frequency of the length mode is $$f = \frac{c}{4L} = \frac{m}{4L}\sqrt{\frac{Y}{\rho}}$$

The value f is resonant frequency, w is the width, a is a constant indicating the number of wavelengths and, is the speed of sound, which is defined by the square root of the Young's modulus (Y) divided by density (ρ). Similar to the width mode, this equation can be validated by constructing 20 PEMS with varying lengths, and measuring the frequency for the first mode of length vibration. The lengths of the cantilevers were measured under a microscope at 6×, and the standard deviation accounts for the fact that the cantilevers were not perfect rectangles and the lengths will vary due to imperfections in the geometry. The resonant frequency is measured using an impedance analyzer, and the standard deviation of the frequency accounts for the variations in Q values and any twinning that might occur in the peak. Only the first length modes are included in the analysis and as a result the value m is set to 1.

Length mode peaks are different from low-frequency flexural modes in that the frequency of the length extension mode can be related to the length of the PEMS as F=c/4l where F is the resonance frequency, c the sound velocity, and l the length of the cantilever. For the first width extension mode and thickness extension mode, the resonance frequencies are related to the width, w and thickness, t as F=c/2w and F=d/2t, respectively. The difference between an extension mode and a flexural mode is that given the same applied ac voltage, the vibration amplitude of an extension mode is much smaller than that of the flexural mode. For example, give an ac voltage amplitude of 0.1V, the vibration amplitude of the first length mode of a 1 mm long PEMS is around one tenth of a nm whereas the vibration amplitude of the first flexural mode is around a hundred nm. Because of the small vibration amplitude involved in a length extension mode, liquid damping does not shift the resonance frequency as much as it does to the low-frequency, high-vibration amplitude of flexural mode, an advantage in in-liquid detection. The present invention can be operated in any of the length, width and thickness extension modes.

To further increase sensitivity and expedite the detection process, the PEMS may be immersed in a flowing solution for in-solution detection. The PEMS is preferably situated in a flow cell system to enable tailored, rapid and simultaneous detection and quantification of multiple organic compounds or molecules.

Figure 1B:
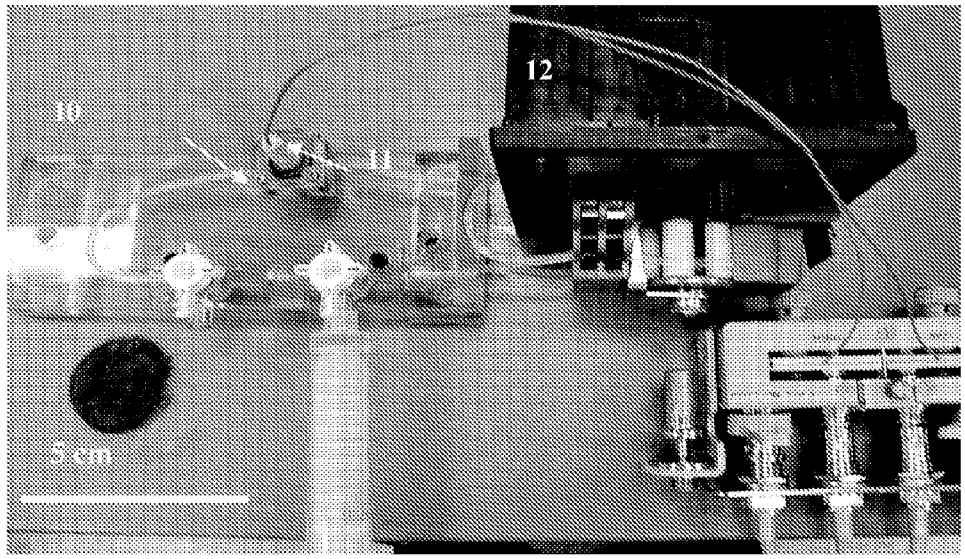
FIG. 1(b) depicts a flow cell system which can be used in conjunction with the cantilevers of the present invention.
Figure 1C:
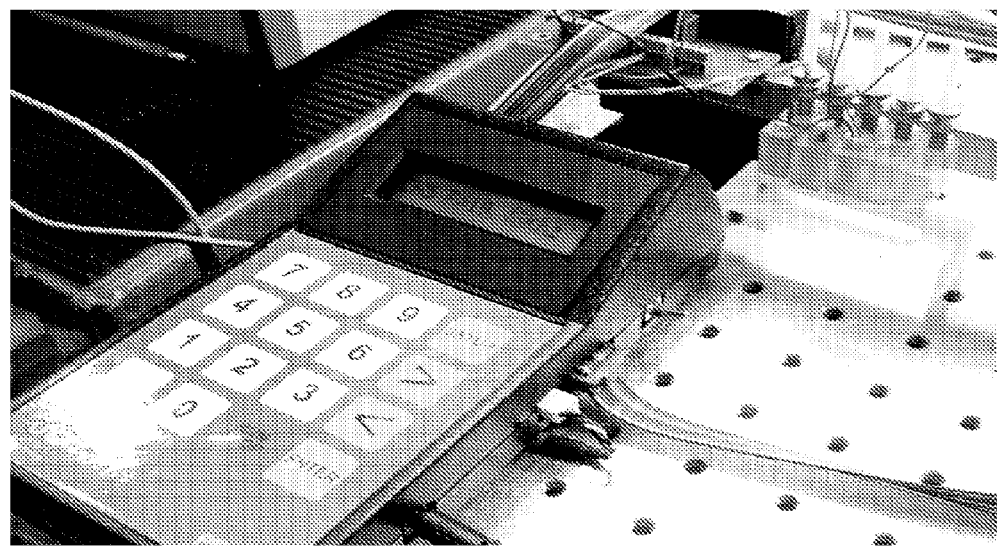
FIG. 1(c) depicts a 3.5 in by 7.5 in portable PEMS sensor capable of working with 8 sensors and powered by a 9-V battery.
Figure 1D:
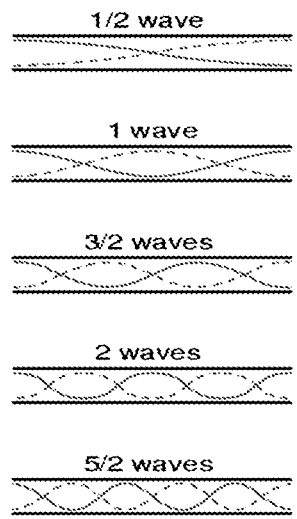
FIG. 1(d) depicts the waves that satisfy the boundary conditions for length mode extension vibrations.

FIG. 1(b) shows a flow cell system 10, with a PEMS holder/measuring unit 11, having a total volume of less than 0.03 ml, pump 12, and a mechanism for controlling temperature and humidity (not shown). The flow cell 10 may attain flow rates of up to 1 ml/min. The total volume of the flow cell, number of channels and flow rate may vary depending upon the number of compounds to be measured. The flow cell 10 may cooperate with a portable PEMS unit, shown in FIG. 1(c), which has multiple channels for the simultaneous quantification of multiple receptor specific molecules. The portable PEMS is inexpensive and capable of obtaining quick measurements.

Another means for further enhancing sensitivity is by increasing humidity. The mass change per unit area per percent humidity change of PZT PEMS is estimated to be about 1.2×10$^{-11}$ g/Hz/mm$^2$/% humidity. The sensitivity of PMN PEMS by comparison is known to be about three times greater than that of PZT PEMS.

The resultant PEMS are chemically inert, thermally stable and miniaturized to enhance sensitivity. They function by binding target molecules that react to the receptors immobilized on the electrodes. The corresponding change in mass shifts the mechanical resonance frequency of the microcantilever. The PEMS is capable of detecting these shifts in resonance frequency by monitoring the $i^{th}$-mode flexural resonance frequency which is related to the effective spring constant, $K_e$, and effective mass, $M_e$, of the piezoelectric cantilever at the tip as shown in Equation 1.

$$f_i = \frac{1}{2\pi}\sqrt{K_e/M_e} \qquad \text{(Equation 1)}$$

The binding of a receptor specific molecule to the cantilever surface changes the cantilever mass and the cantilever spring constant. The resonance frequency shift Δf, expressed in Equation 2, $$\Delta f_i = f_i \left( -\frac{\Delta m}{2M_e} + \frac{\Delta k}{2K_e} \right), \quad \text{(Equation 2)}$$

where Δm and Δk denote the mass change and the effective spring constant, model the functionality of the microcantilever. Reducing the PEMS thickness and dimension binding-related stress greatly enhances the resonance frequency shift.

In operation, an alternating voltage may be applied to conductive element 1 to drive piezoelectric layer 7 of the self-actuating PEMS and a conductive element 2 may be used to detect a shift in the mechanical resonance frequency of the PEMS due to the binding of a target molecule or compound by the receptors. During this process, the method of the present invention involves inducing a positive or negative change in the Young's modulus of the piezoelectric layer, which is preferably a substantial change in the Young's modulus of the piezoelectric layer. In one exemplary embodiment, the change in the Young's modulus may be up to about 70%. The change in the Young's modulus of the piezoelectric layer is preferably greater than about 25%. Most preferably, the change in the Young's modulus may be about 25% to about 70%. One of the factors that induces a change in the Young's modulus is non-180° polarization domain switching.

By inducing and/or enhancing non-180° polarization domain switching, it may be possible to further increase the detection sensitivity of the PEMS in comparison to non-piezoelectric or weak piezoelectric microcantilevers of the same dimension. One means for inducing non-180° polarization domain switching may be application of stress produced by the binding of target molecules or compounds. In another exemplary embodiment, non-180° polarization domain switching may be induced by exposing the PEMS to a DC bias electric field. The DC bias electric field may be established using any conventional means and may involve applying a DC voltage across a thickness, length or width of piezoelectric layer 7. Preferably, the established DC bias electric field (E) is from about −20 kV/cm to about 20 kV/cm, more preferably, from about −10 kV/cm to about 10 kV/cm, and, most preferably, from about −8 kV/cm to about 10 kV/cm. A positive value for E denotes an applied electric field that is parallel to the poling direction of the piezoelectric layer. A negative value for E denotes an applied electric field that is opposite to the poling direction of the piezoelectric layer. By establishing a DC bias electric field, the flexural frequency shift and hence, detection sensitivity, may be further increased by a factor of up to about three in comparison to the sensitivity PEMS operated without a DC bias electric field. The DC bias electric field changes the polarization configuration such that it increases polarization domain switching, which in turn enhances the resonance frequency shift enabling enhanced detection sensitivity. The degree of detection sensitivity enhancement is dependent upon the piezoelectric material, the thickness of the piezoelectric layer, whether it is bonded to a non-piezoelectric layer, the physical properties, i.e. thickness and/or material characteristics of the non-piezoelectric layer and any combination thereof.

The method may further involve enabling detection of a species of interest using any resonance frequency peak and any resonance frequency modes. In an exemplary embodiment, the PEMS may be operated in a flexural resonance mode, a longitudinal resonance mode, such as a length mode, a width mode and/or a thickness mode, or a combination thereof. Preferably, the PEMS may be capable of length-mode and width-mode detection, which enables more sensitive detection with high peak frequency intensities and minimized damping effects. More preferably, the PEMS is capable of enhanced detection sensitivity using both flexural and longitudinal resonance modes. In an exemplary embodiment, the PEMS may be used at resonance frequencies within the range of about 10 kHz to about 10 GHz.

The present invention is generally applicable for the investigation and study of, for example, protein-protein and protein-mRNA interactions. This is an important step towards understanding the physiological metabolic pathways. A key parameter that characterizes the strength of protein-protein or protein-mRNA interactions is the equilibrium dissociation constant, $K_d$ (in units of molar (M)) between the two molecules which can be determined using the method of the present invention.

The invention is applicable to, for example, antigen and antibody interactions. The specific association of antigens and antibodies is dependent on intermolecular forces between antigen and antibody such as hydrogen bonds, hydrophobic interactions, electrostatic forces, and van der Waals forces. These are all noncovalent bonds, but can be quite strong, with interaction forces ranging from 10 to 100 pN. All antigen-antibody binding is reversible, however, and follows the basic thermodynamic principles of any reversible bimolecular interaction:

$$K_d = \frac{k_d}{k_a} = \frac{[Ab][Ag]}{[Ab-Ag]} \quad (3)$$

where $K_d$ is the dissociation constant, [Ab] and [Ag] are the molar concentrations of unoccupied binding sites on the antibody or antigen respectively, and [Ab-Ag] is the molar concentration of the antibody-antigen complex. The time taken to reach equilibrium is dependent on the rate of diffusion and the affinity of the antibody for the antigen, and can vary widely. The affinity constant for antibody-antigen binding can span a wide range, extending from below $10^5$ mol$^{-1}$ to above $10^{12}$ mol$^{-1}$. Affinity constants can be affected by temperature, pH and solvent. Affinity constants can be determined for monoclonal antibodies, but not for polyclonal antibodies, as multiple bonds form between polyclonal antibodies and their antigens. The equilibrium constant of a receptor is a thermodynamic property, and the measured value should be independent of the measurement procedure providing the act of measurement does not damage the receptor, and the experimental conditions (temperature, pH, ionic strength, etc) are maintained.

The invention is also applicable to DNA hybridization as well as physical desorption of gases. In each case, the dissociation constant, Kd, can be determined using the method of the present invention. In each case, appropriate receptors are selected for immobilization on the cantilever sensor and the same methodology is employed as for determining the dissociation constant for protein-protein and protein-RNA interactions. Suitable receptors may include, for example, a complementary strand of DNA or a substrate that allows reversible adsorption of a particular gas. Skilled persons can choose a suitable receptor for a particular reaction to determine the dissociation constant.

The invention is directed to a method for determining the dissociation constant ($K_d$) by plotting resonance frequency shift as a function of time for various target analyte concentrations. From this graph, the fraction of saturation, i.e. equilibrium fraction of bound binding sites out of all available binding sites on the sensor surface may be estimated by taking the ratio of the equilibrium resonance frequency shift at a selected concentration to the equilibrium frequency shift of the sensor. The dissociation constant is the inverse slope of the line produced by graphing the fraction of saturation as a function of concentration.

For obtaining a resonance frequency shift, the piezolelectric microcantilever sensor (PEMS) is contacted with the target analyte, for example, using a flow cell. Other suitable, conventional methods for contacting the PEMS with the target analyte are also possible and within the scope of the present invention.

The resonance frequency shift of the PEMS sensor is then determined as a function of time for a plurality of known target analyte concentrations. An equilibrium frequency shift of the sensor can be determined by plotting the resonance frequency shift versus time and identifying when the equilibrium condition has been reached, e.g. when the frequency shift stabilizes. The sensor is also calibrated to determine its equilibrium frequency shift in the absence of the analyte so as to provide a baseline for the determination.

From this information, the fraction of saturation ($\theta$) may be accurately estimated by taking the ratio of the equilibrium resonance frequency shift at a selected concentration to the equilibrium frequency shift of the sensor. The dissociation constant may then be determined by calculating the inverse slope of the line produced by graphing the fraction of saturation as a function of the plurality of known analyte concentrations.

The present method provides a reliable, easily implemented method for the determination of dissociation constants which employs relatively inexpensive equipment and can be carried out in real-time.

EXAMPLES

Example 1

Figure 2:
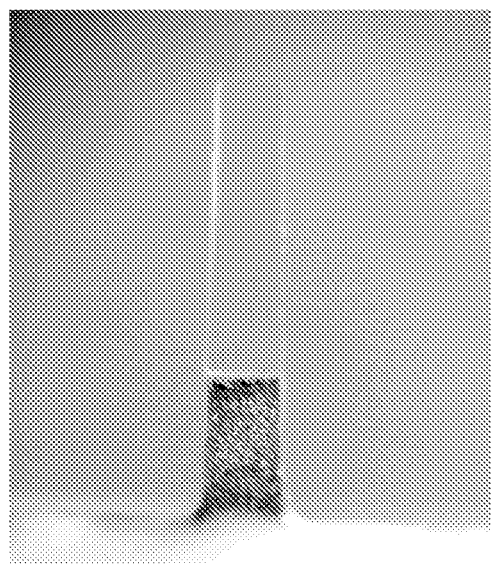
FIG. 2 is an optical micrograph of the PZT/glass PEMS of Example 1 of the present application.
Figure 3:
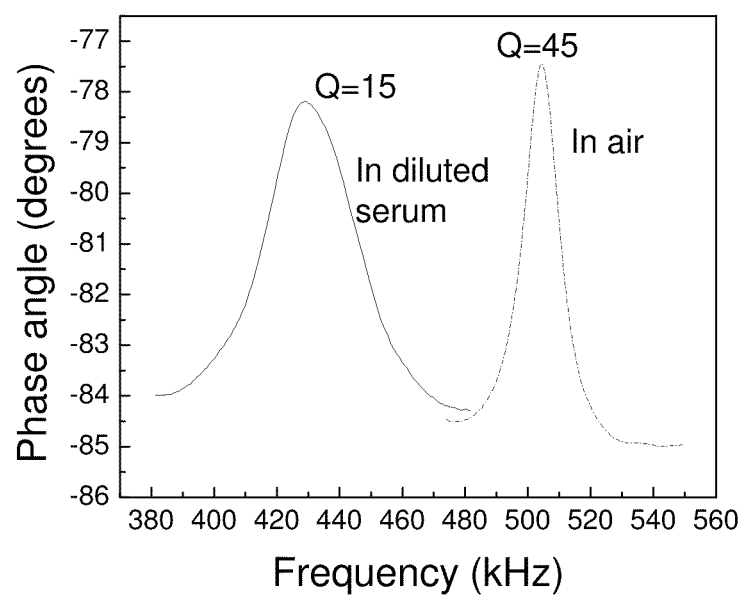
FIG. 3 shows in-air and in-liquid resonance spectra of the PZT/glass PEMS which was 970 μm long and 580 μm wide with an 1800 μm long glass tip used in Example 1 of the present application.

The PZT/glass PEMS used in this study consisted of a commercial PZT layer (T105-H4E-602, Piezo System, Cambridge, Mass.) 127 µm thick, 970 µm long and 580 µm wide bonded to a 75 µm thick glass layer (Fisher Scientific, Pittsburgh, Pa.) with a 1.8 mm long glass tip protruding from the free end. The PEMS was fabricated by first bonding the PZT layer to the glass layer using a nonconductive epoxy (Loctite, Rocky Hill, Conn.) and embedding the PZT/glass bilayer in wax. The PZT/glass bilayer was then cut to strips with a wire saw (Princeton Scientific Precision, Princeton, N.J.). After attaching the wires to the top and bottom electrodes using conductive glue (XCE 3104XL, Emerson and Cuming Company, Billerica, Mass.), a PZT/Glass strip was glued to a glass substrate to form the microcantilever shape. An optical micrograph of the PZT/glass PEMS is shown in FIG. 2. The resonance peak used for this detection was the first longitudinal extension mode at around 504 kHz in air with a Q value of 45 and around 429 kHz in diluted serum with a Q value of 15 as shown in the resonance spectra in FIG. 3.

For the initial 3-mercaptopropyltrimethoxysilane (MPS) deposition, the PEMS were first cleaned in a diluted (1:100 in water) piranha solution (two parts of 98% sulfuric acid (Fisher, Fair Lawn, N.J.) with one part of 30% hydrogen peroxide (FisherBiotech, Fair Lawn, N.J.)) at 20° C. for 1 minute followed by soaking in a 40 mM MPS solution in ethanol covered with paraffin film for 4 hours and rinsing by de-ionized (DI) water. They were then soaked in a 0.01 M NaOH solution overnight for cross-linking, followed by soaking in DI water for 1 hour and overnight vacuum-oven drying (Model 1400E, VWR International) at 762 mm Hg to conclude the first MPS coating. For each of the subsequent MPS depositions, they were soaked overnight in a freshly prepared 40 mM MPS solution in ethanol titrated to pH=4.5 with acetic acid. This procedure was repeated two times to give a total of 3 MPS depositions to provide an MPS thickness of about 150 nm.

The target Her2 extracellular domain (ECD) was expressed from stably-transfected HEK-293 cells and purified using immobilized metal affinity chromatography (IMAC) in a conventional manner. The anti-Her2 scFv, H3, was isolated from a naïve human scFv phage display library using conventional techniques. Her2 ECD obtained as described above was coated onto a Maxisorp-Immunotube (NUNC, Denmark) at a concentration of 20 µg/mL in coating buffer (Bup-H carbonate bicarbonate buffer; Pierce) at 4° C., overnight. scFv-Phage library stock (100 µL; $1.3 \times 10^{13}$ pfu/mL) was added to the immunotubes to pan (isolate) anti-Her2 scFv-phage clones. The H3 clone was isolated following four rounds of selection, was sequenced and subcloned into the pCyn expression vector. Soluble scFv were expressed in *E. coli* TG1, isolated from the periplasmic space and purified by Ni-NTA agarose affinity chromatography and HPLC on a Superdex75 column (Pharmacia). Final yields were 1-2 mg of pure H3 scFv per liter of expression culture. Specificity for Her2 ECD was confirmed by surface plasmon resonance on a BIAcore 1000 instrument and by flow cytometry against Her2 overexpressing human tumor cell lines.

Sulfosuccinimidyl-4-(N-maleimidomethyl)cyclohexane-1-carboxylate (sulfo-SMCC) (Pierce) was used as the bi-functional linker for scFv immobilization on MPS. First, the scFv was linked to sulfo-SMCC using a 1 ml solution 900 nM scFv and 80 µM sulfo-SMCC for 2 hr at 4° C. The NHS-ester in the sulfo-SMCC will react with a primary amine of the scFv. Unreacted sulfo-SMCC molecules were then removed by repeating microcentrifugation at 6000 RPM with a 10 kD filter (Millipore) three times. The MPS-coated PEMS was then soaked in the sulfo-SMCC-linked scFv solution with 5 mM ethylenediaminetetraacetic acid (EDTA) (Pierce) for 2 hr to immobilize the scFv on the MPS coating surface via the reaction of the maleimide of the sulfo-SMCC with the sulf-hydryl of the MPS. The adsorption density, F, of the SMCC-linked scFv on the MPS was estimated to be $\Gamma=7$ ng/mm$^2$. from a separate measurement using a quartz crystal microbalance.

A human serum typically contains about 40 mg/ml of albumin which helps maintain the blood osmotic pressure to prevent leaking of the fluid from the blood to tissues. Albumin is by far the most abundant protein in serum and the major source of potential non-specific binding. To minimize potential non-specific binding in diluted serum (1) the detection was carried out in 1 in 40 diluted human serum (one part of human serum with 40 parts of PBS, and (2) the sensor surface was blocked with a 30 mg/ml BSA (Bovine serum Albumin) solution in PBS prior to detection.

For Her2 detection, the scFv-immobilized PEMS was then immersed in a home-built flow cell with a peristaltic pump (model 77120-62, Cole-Parmer's Master Flex, Vernon Hills, Ill.) for both BSA blocking and Her2 detection with the PEMS's two faces tangential to the flow at a flow rate of 0.7 ml/min. The flow cell contained 6 ml of liquid.

Figure 4:
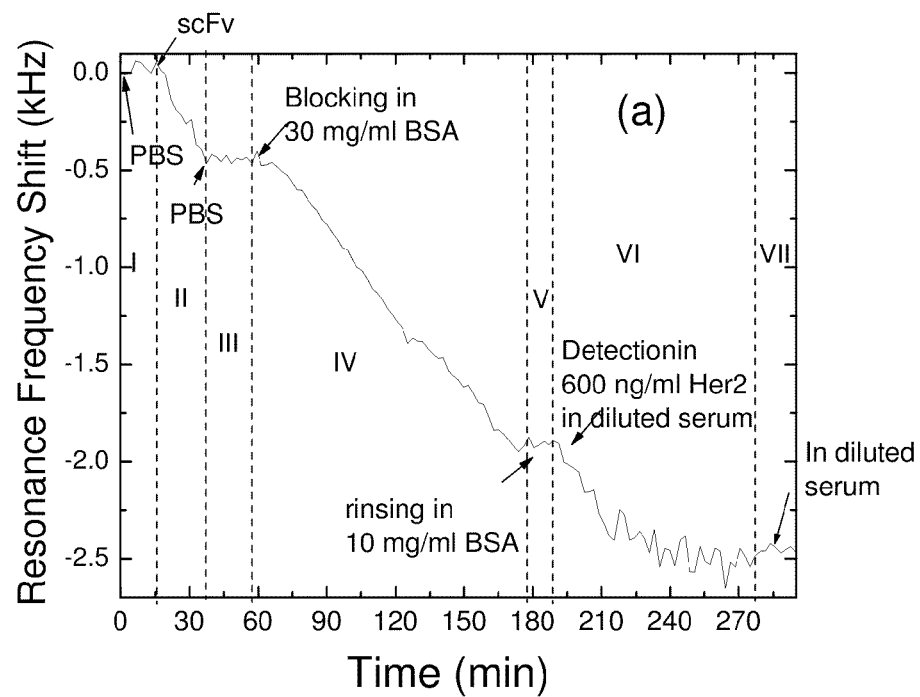
FIG. 4 shows the resonance frequency shift versus time of the PEMS: in PBS in period I at t=0-15 minutes, scFv immobilization in period II at 15-44 minutes, PBS rinsing in period III at 43-59 minutes, 30 mg/ml BSA blocking in period IV at 59-185 minutes, 10 mg/ml BSA rinsing and Tween20 rinsing in period V, detection in 600 ng/ml Her2 in 1 in 40 diluted serum in period VI at t=185-278 minutes and rinsing in diluted serum in period VII at t=278-300 minutes for Example 1.

To illustrate the real-time nature of the PEMS, after the scFv was chemically bonded to SMCC as described above, the MPS-coated PEMS was then placed in the flow cell and subjected to scFv immobilization, BSA blocking, and Her2 detection at a flow rate of 0.7 ml/min. The resonance frequency shift versus time in this sequence is shown in FIG. 4. It started with immersing the PEMS in PBS for 15 minutes in period I at t=0-15 min. As can be seen, during this period, the resonance frequency of the PEMS remained at 0±30 Hz.

This PBS period was followed with the immobilization of the SMCC-linked scFv in period II at t=15-44 minutes in which the resonance frequency of PEMS decreased with time, yielding a resonance frequency shift of roughly −430 Hz at t=44 min. After the scFv immobilization procedure, PBS was then flown for 15 minutes in period III at t=44-59 minutes to remove any unbound scFv from the flow cell. During this second PBS period, the shift in resonance frequency was 0±25 Hz, again indicating that the resonance frequency of PEMS was stable with time in PBS. Between t=59 minutes to 185 minutes in period IV, a 30 mg/ml BSA solution in PBS was flown in the flow cell to preemptively saturate the unoccupied sites on the sensor surface with BSA to minimize potential non-specific binding later in the Her2 detection in diluted human serum.

The resonance frequency shift due to the non-specific BSA binding to the unoccupied sites saturated at around t=172 minutes, yielding a net resonance frequency shift of about -1470 Hz. Following the BSA blocking, the PEMS was rinsed with a 10 mg/ml BSA and 0.1% Tween20 solution in period V at t=185-195 minutes. Again, during this rinsing period, the resonance frequency of the PEMS remained fairly stable throughout. The PEMS was then exposed to the flow of diluted human serum containing 600 ng/ml of Her2 in period VI at t=185-278 minutes over which period the PEMS exhibited a resonance frequency shift of −520 Hz. A final background check of flow of diluted serum was conducted in period VII at t=278-295 minutes. As can be seen, in period VII, the resonance frequency of the PEMS also remained stable in diluted serum after the detection.

Figure 5:
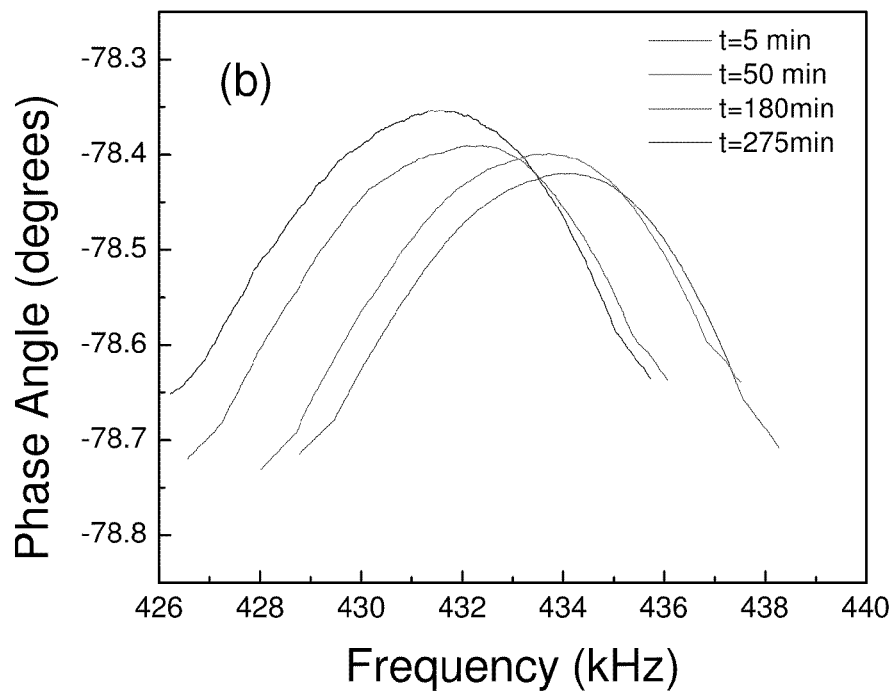
FIG. 5 shows the phase angle versus frequency resonance spectra at t=5 minutes (in PBS), 50 minutes (after scFv immobilization), 180 minutes (after BSA blocking), and 275 minutes (after Her2 detection). Throughout the detection period, the shape of the resonance peak and the Q value remained constant for Example 1.

To show that the resonance frequency shifts shown in FIG. 4 at various times were indeed reliable, the phase angle versus frequency resonance spectra of the PEMS is shown at t=5 minutes in PBS, at t=50 minutes after the scFv immobilization, at t=180 minutes after the BSA blocking, and at t=275 minutes after the Her2 detection during the above test in FIG. 5. As can be seen, the shape and height of the resonance peak remained roughly constant throughout the test, indicating that the resonance frequency shifts shown in FIG. 4 were indeed reliable.

Example 2

To find out the detection concentration limit of the longitudinal extension mode of the PZT/glass PEMS, the dose response of Her2 in diluted human serum was examined. Before each detection step the PEMS was stripped of the bound scFv and reinsulated with MPS. Fresh scFv was then immobilized on the PEMS surface using procedures as described above. The PEMS was then subjected to a PBS flow across the PEMS surface for 10 minutes to establish the background followed by 30 mg/ml BSA blocking in a flow until the resonance frequency of the PEMS saturated (about 2 hours) followed by rinsing with 10 mg/ml BSA and 0.1% Tween 20. The PEMS was then exposed to diluted human serum spiked with Her2 in one of the following concentrations: 60,000, 6,000, 600, 60, and 6 ng/ml. In this study, the scFv was immobilized after each detection step as opposed to simply releasing the Her2 in a glycine/HCl buffer solution after detection to ensure that the binding performance of the scFv in each detection step was roughly identical.

Figure 6:
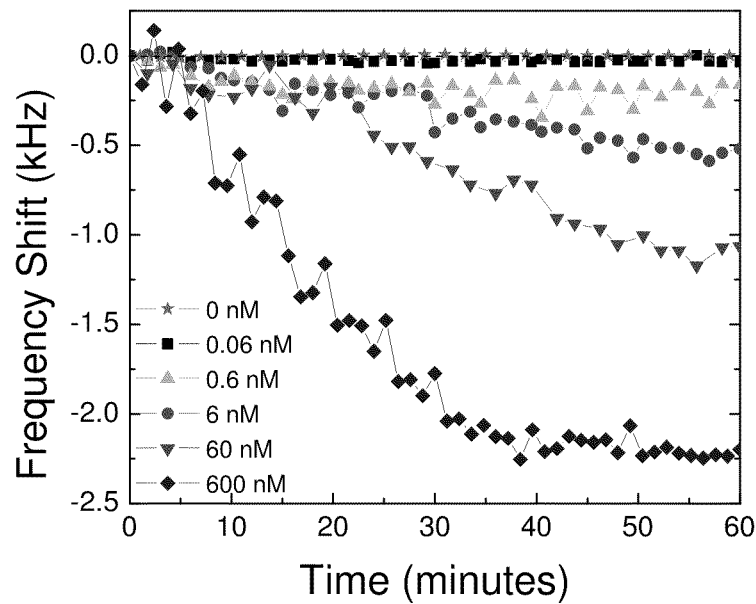
FIG. 6 shows the resonance frequency shift versus time of the PEMS in diluted serum spiked with 0 nM (stars), 0.06 nM (squares), 0.6 nM (up triangles), 6 nM (circles), 60 nM (down triangles), and 600 nM (diamonds) of HER2 for Example 2.

The obtained resonance frequency shift versus time in diluted serum with 60,000, 6,000, 600, 60, 6, and 0 ng/ml (corresponding to 600, 60, 6, 0.6, 0.06, and 0 nM) of Her2 is shown in FIG. 6 where each curve was the average of two independent tests. As can be seen, at t=60 minutes, the PEMS yielded a resonance frequency shifts of 2250±120, −1060±170, −531±110, −160±150, −35±15, and 0±15 Hz in diluted serum with 60,000, 6,000, 600, 60, 6 and 0 ng/ml of Her2, respectively. Note that at 0 ng/ml of Her2 in diluted serum, the PEMS exhibited no net shift in resonance frequency throughout the 60 minutes of exposure with a standard deviation of about 15 Hz. The 35±15 Hz shift at t=60 minutes at 6 ng/ml seemed well above the standard deviation of the control (15 Hz) or that at 6 ng/ml (also 15 Hz). The reason for the slow, almost linear response over the 60 minutes of detection at this concentration was in part due to the low concentration of 6 ng/ml as well as the moderately low affinity of this scFv. It is also worth noting that the noise level (standard deviation) was considerably higher at a higher Her2 concentration: 120, 170, 110, 150 at 60,000, 6,000 600, 60 ng/ml of Her2, respectively as opposed to 15 Hz at 6 and 0 ng/ml of Her2. The same trend has been observed in in-situ detection of other biological systems, indicative that the noise during detection was likely related to binding, unbinding and re-arrangement of the antigen on the sensor surface.

Figure 7:
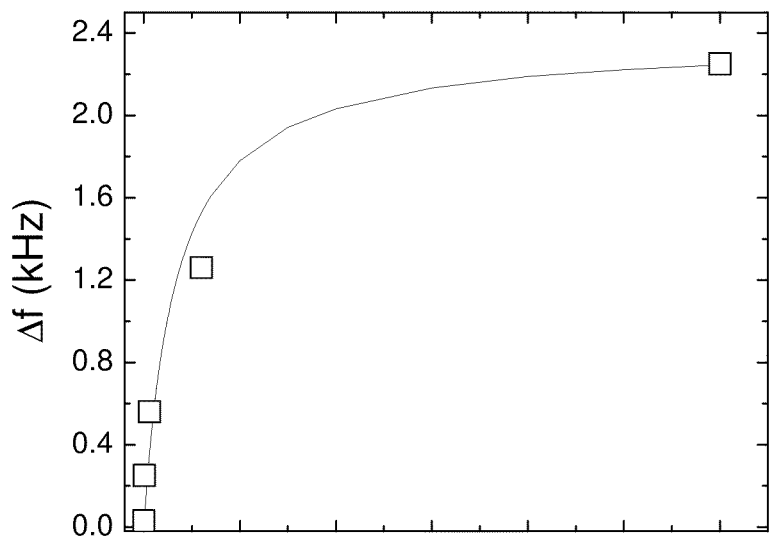
FIG. 7 shows a plot of equilibrium resonance frequency shift as approximated by the resonance frequency shift at t=60 minutes versus Her2 concentration, c for Example 2.

As can be seen from FIG. 6, at t=60 min, the resonance frequency shifts at all concentrations appeared saturated. It is therefore reasonable to assume that the resonance frequency shifts at t=60 minutes as equilibrium resonance frequency shift at theses Her2 concentrations. Therefore, in FIG. 7, equilibrium resonance frequency shift is plotted as approximated by the resonance frequency shift at t=60 minutes versus Her2 concentration, c.

Because the preliminary $K_d$ obtained by earlier BIAcore studies was $3.4 \times 10^{-8}$ M, which was about 18 times smaller than the concentration of 600 nM at 60,000 ng/ml, we thus approximated the t=60 min resonance frequency shift, −2250 Hz at this concentration shown in FIG. 6 as the equilibrium saturated resonance frequency shift, $\Delta f_s$. The fraction of saturation, $\theta$, which is defined as the equilibrium fraction of bound binding sites out of all available binding sites on the sensor surface can be estimated as the ratio of the equilibrium resonance frequency shift $\Delta f(c)$ at concentration, c to $\Delta f_s$. Approximating the resonance frequency shift at t=60 min at concentration, c as the equilibrium $\Delta f(c)$, the equilibrium fraction of saturation can then be deduced as $\theta = \Delta f(c)/\Delta f_s$. The obtained $\theta$ versus c is plotted as open squares in FIG. 8. The equilibrium dissociation constant, $K_d$ is related to the Her2 concentration, c, as $$\theta = \frac{c/K_d}{1+c/K_d}, \quad (4)$$

As can be seen from Eq. (4), at low concentrations, $\theta$ is linear to c with a slope that is the inverse of $K_d$. In FIG. 9, c versus $\theta$ is plotted for the concentrations below 6 nM where $\theta$ was less than 0.25. By approximating the slope of c versus $\theta$ of FIG. 9 to be $K_d$, the following equation was obtained: $K_d = 3.0 \pm 0.3 \times 10^{-8}$ M. Using the obtained $K_d$, $\theta$ was calculated for all concentrations and the calculated $\theta$ was plotted as the solid line in FIG. 8. As can be seen, the solid line agreed well with the experimental data points, indicating the deduced $K_d$ was reasonable. Based on the calculated $\theta$, a theoretical resonance frequency shift curve is also plotted in FIG. 7 as a solid line. Similar to FIG. 8, the solid line also agreed with the experimental data.

The binding kinetics of H3 scFv to Her2 were also examined using a BIAcore 1000 instrument (BIAcore, Piscataway, N.J.) using recombinant Her2 bound to a CM5 sensor chip with epidermal growth factor receptor (EGFR) bound to a different CM5 sensor chip as the reference. The response of the BIAcore was recorded at H3 scFv concentrations 150 nM and 76 nM across the Her2 and EGFR chips, respectively, and the results are shown in FIG. 10. The response measured from the EGFR chip was used as an assessment of the background and was subtracted from the response measured for the Her2 chip. The response of the Her2 chip after the background correction is shown in FIG. 11. Sections of the curve associated with H3 binding and unbinding were then fitted to the following equation:

$$\frac{dR}{dt} = k_a c (R_{max} - R) - k_d R, \quad (5)$$

where R and $R_{max}$ were the response signal and the maximum response signal at saturation, respectively, t the time, c the H3 concentration, and $k_a$ and $k_d$ were the association and dissociation rate constants, respectively. The value for $k_a$ was deduced to be $2.3 \times 10^5$ $M^{-1}s^{-1}$ and $k_d$ to be $6.8 \times 10^{-3}$ $s^{-1}$. Using these values, the equilibrium dissociation constant $K_d = k_d/k_a$ was deduced to be $3 \times 10^{-8}$ M, in agreement with the $3 \pm 0.3 \times 10^{-8}$ M obtained by the PEMS.

In addition to obtaining $K_d$ from $k_a$ and $k_d$ as deduced from the adsorption and desorption sections of the BIAcore curves, the fractional equilibrium response, θ, used in Eq. (4) could also be obtained as the ratio of the equilibrium response, R, to the maximum response $R_{max}$, as $R/R_{max}$. With $R_{max}=308$ RU, the values of θ were determined to be 0.83 and 0.74 for 150 nM and 76 nM, respectively. These values were also plotted in FIG. 8 as full circles. Clearly, the full circles from the BIAcore measurements fell on the solid line deduced by the PEMS results, indicating the agreement of the $K_d$ value determined from BIAcore based on the fractional equilibrium response with the results obtained with the PEMS. The deduced $K_d$ value from the BIAcore data by fitting to Eq. (4) was also $3 \times 10^{-8}$ M, again, in agreement with the PEMS result of $3 \pm 0.3 \times 10^{-8}$ M. In addition, the $Chi^2$ parameter of the present BIAcore measurements was 6 and was smaller than 10, which indicates that the values for $k_a$, $k_d$, $K_d$ deduced from the BIAcore were statistically valid, further conforming the validity of the $K_d$ value determined by the PEMS.

Real-time, label-free, in-situ detection of Her2 in diluted serum using a PZT/glass PEMS with H3 scFv immobilized on the MPS insulation layer of the PEMS surface was demonstrated. It was shown that the PEMS could detect Her2 at a concentration of 6 ng/mL in diluted human serum. Furthermore, using the detection results at 0.6, 6, and 60 nM of Her2 in diluted serum, a dissociation constant, $K_d$, of $3.3 \times 10^{-8}$ M was deduced and confirmed as being consistent with that obtained by use of a conventional BIAcore device.

Example 3

Figure 12A:
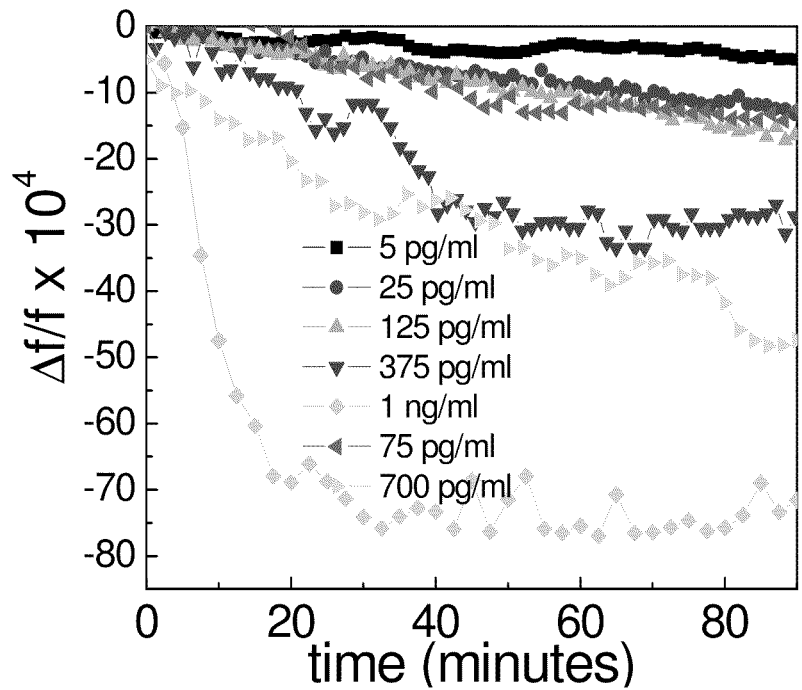
FIG. 12(a) depicts the normalized frequency for the L26 antibody at concentrations of Her2 ranging from 5 pg/ml to 1 ng/ml spiked in human serum diluted 1:40 in PBS.
Figure 12B:
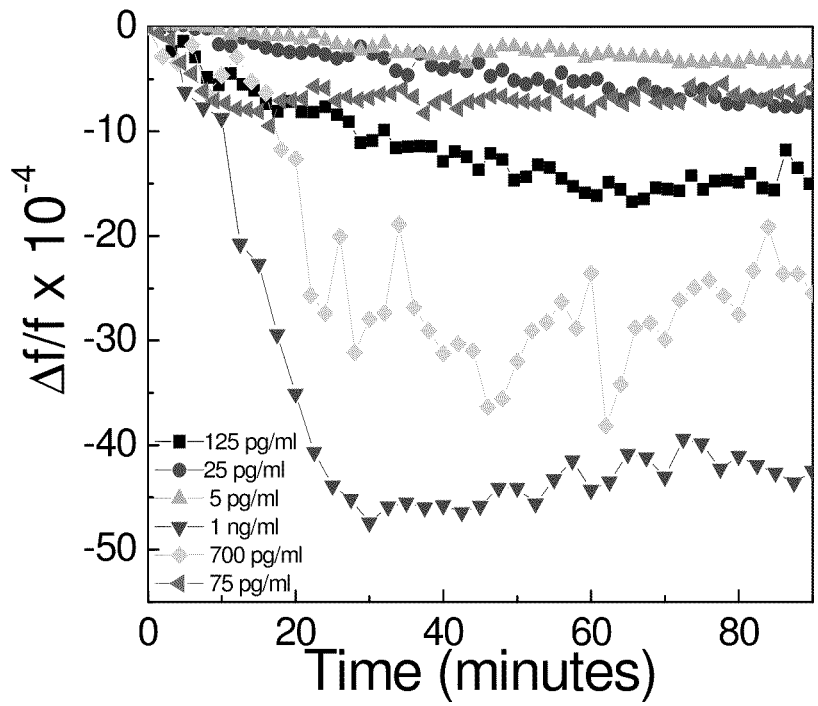
FIG. 12(b) depicts the normalized frequency for Herceptin at concentrations of Her2 ranging from 5 pg/ml to 1 ng/ml spiked in human serum diluted 1:40 in PBS.
Figure 13A:
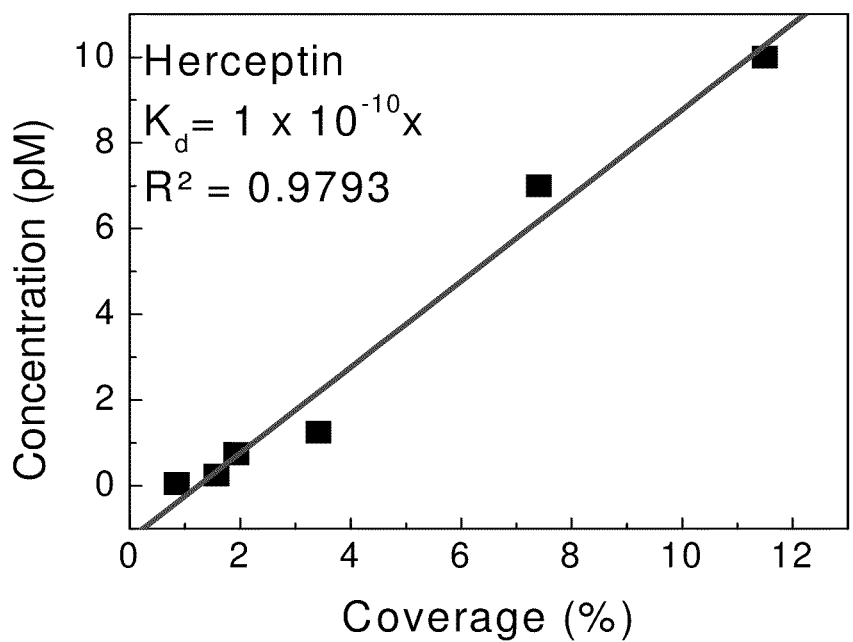
FIGS. 13(a)-13(b) show the inverse of the slopes of the best fit lines of Herceptin in FIG. 13(a) and the L-26 antibody in FIG. 13(b) from which the $K_d$ can be determined.
Figure 13B:
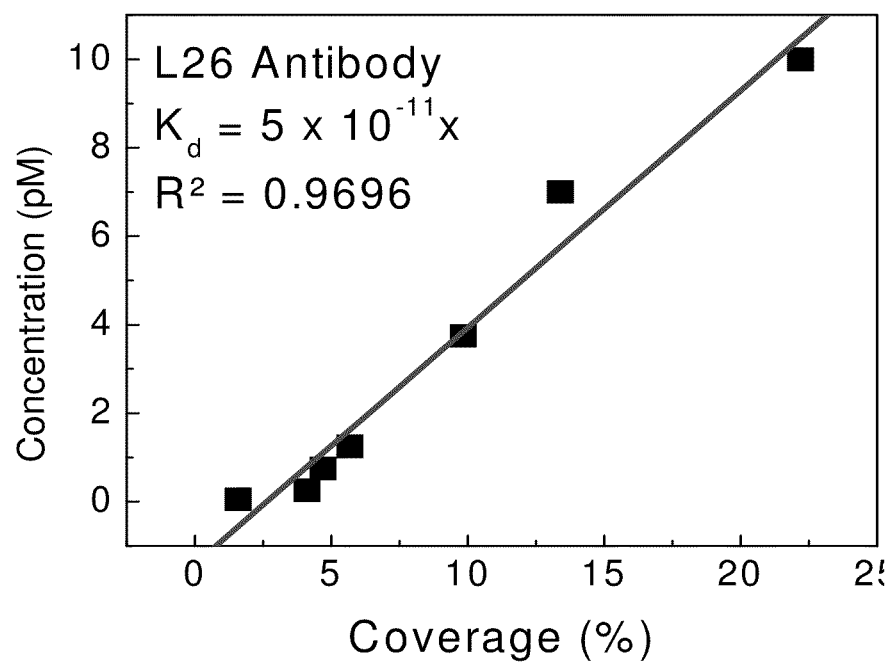

Using the dose response curves of FIGS. 12(a)-12(b) and calibration curves for Herceptin and L26, the dissociation constant can be determined using the Langmuir isotherm. Using the measured maximum relative frequency shifts ($\Delta f_s/f$) $4 \times 10^{-2}$ and $3.23 \times 10^{-2}$ for Herceptin and L26, respectively, value of coverage, θ, can be deduced and plotted as a function of Her2 concentration. FIGS. 13a-13b depict the graphs of coverage vs. Her2 concentration. Using a linear regression, the inverse of slope of the best fit line will be the equilibrium constant $K_d$. The coefficients of determination for the best fit lines indicate a good fit as the value for Herceptin is 0.98 and L-26 is 0.97. The $K_d$ deduced for Herceptin is 0.1 nM, which is in agreement with those found in the literature. The value of $K_d$ deduced for the L-26 antibody is 0.5 nM. However there is currently no value listed in the literature which the deduced value can be compared. The accuracy of the measurement of equilibrium constant can be used to further validate the accuracy of the PEMS.

The foregoing examples have been presented for the purpose of illustration and description only and are not to be construed as limiting the scope of the invention in any way. The scope of the invention is to be determined from the claims appended hereto.

What is claimed is:

1. A method for determining a dissociation constant using a piezoelectric sensor comprising the steps of:
    obtaining an equilibrium resonance frequency shift of the piezoelectric sensor as a function of time for each of a plurality of target analyte concentrations;
    determining a fraction of saturation from a ratio of the equilibrium resonance frequency shift at each concentration of said target analyte to an equilibrium resonance frequency shift of the piezoelectric sensor obtained in the absence of said target analyte; and
    determining an inverse slope of a line produced by graphing the determined fraction of saturation as a function of target analyte concentration, wherein the inverse slope is a dissociation constant.

2. A method as claimed in claim 1, wherein the sensor is a piezoelectric microcantilever sensor.

3. A method as claimed in claim 2, wherein the target analyte is selected from the group consisting of proteins, DNA, gases and mRNA's.

4. A method as claimed in claim 2, wherein the target analyte comprises a protein and the dissociation constant is determined for a protein-protein interaction.

5. A method as claimed in claim 2, wherein the target analyte comprises an mRNA.

6. A method as claimed in claim 2, wherein the target analyte is selected from the group consisting of antigens and antibodies.

7. A method as claimed in claim 2, wherein the dissociation constant is determined for gas desorption.

8. A method as claimed in claim 2, wherein the dissociation constant is determined for DNA hybridization.

9. A method as claimed in claim 2, wherein the piezoelectric microcantilever sensor is operated in a flexural mode.

10. A method as claimed in claim 2, wherein the piezoelectric microcantilever is operated in an extension mode.

11. A method as claimed in claim 10, wherein the piezoelectric microcantilever is operated in a width extension mode.

12. A method as claimed in claim 10, wherein the piezoelectric microcantilever is operated in a length extension mode.

13. A method as claimed in claim 10, wherein the piezoelectric microcantilever is operated in a thickness extension mode.

14. A method as claimed in claim 2, wherein the resonance frequency shift of the piezoelectric microcantilever sensor results from a change in the Young's modulus of a piezoelectric layer of the piezoelectric microcantilever sensor caused by binding of an immunological response factor to receptors on said piezoelectric microcantilever sensor inducing non-180° polarization domain switching in said piezoelectric layer.

15. The method of claim 14, wherein a DC bias electric field is applied to said microcantilever sensor during said obtaining step.

* * * * *